US 8,682,045 B2

(12) United States Patent
Vining et al.

(10) Patent No.: US 8,682,045 B2
(45) Date of Patent: *Mar. 25, 2014

(54) VIRTUAL ENDOSCOPY WITH IMPROVED IMAGE SEGMENTATION AND LESION DETECTION

(75) Inventors: David J. Vining, Winston-Salem, NC (US); Gordon W. Hunt, Winston-Salem, NC (US); David K. Ahn, Winston-Salem, NC (US); David R. Stelts, Rock Hill, SC (US); Yaorong Ge, Winston-Salem, NC (US); Paul F. Hemler, Winston-Salem, NC (US); Tiffany W. Salido, Cullowhee, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 833 days.

This patent is subject to a terminal disclaimer.

(21) Appl. No.: 12/826,268

(22) Filed: Jun. 29, 2010

(65) Prior Publication Data
US 2010/0265251 A1 Oct. 21, 2010

Related U.S. Application Data

(63) Continuation of application No. 09/856,683, filed as application No. PCT/US99/28030 on Nov. 24, 1999, now Pat. No. 7,747,055, application No. 12/826,268, which is a continuation-in-part of application No. 09/299,061, filed on Apr. 23, 1999, now Pat. No. 6,366,800, which is a continuation of application No. 08/805,584, filed on Feb. 25, 1997, now Pat. No. 5,920,319.

(60) Provisional application No. 60/109,966, filed on Nov. 25, 1998.

(51) Int. Cl.
G06K 9/00 (2006.01)

(52) U.S. Cl.
USPC .............................. 382/128; 382/154; 378/1

(58) Field of Classification Search
None
See application file for complete search history.

(56) References Cited

U.S. PATENT DOCUMENTS

| 4,243,652 | A | 1/1981 | Francis |
| 4,315,309 | A | 2/1982 | Coli |

(Continued)

FOREIGN PATENT DOCUMENTS

| AU | 706280 | 9/1999 |
| AU | 777440 | 3/2001 |

(Continued)

OTHER PUBLICATIONS

Official Action dated Oct. 1, 2009 for U.S. Appl. No. 11/157,136.
Official Action dated Nov. 13, 2008 for U.S. Appl. No. 11/157,136.
Official Action dated Feb. 5, 2009 for U.S. Appl. No. 11/637,207.
Official Action dated Dec. 8, 2009 for U.S. Appl. No. 11/637,207.
Noboru Maki, "Image Processing Expanding Particularly in the Medical and the Mapping Fields", Nikkei Computer Graphics, Jan. 1990, p. 63 (English translation: Transmittal No. 574154).
Jolesz, F.A., et al., "Interactive Virtual Endoscopy", Amerial Journal of Roentegenology, V. 169, 1997, pp. 1229-1235.

(Continued)

Primary Examiner — Manav Seth
(74) Attorney, Agent, or Firm — Niels Haun; Dann, Dorfman Herrell & Skillman, PC

(57) ABSTRACT

A system, and computer implemented method are provided for interactively displaying three-dimensional structures. Three-dimensional volume data (34) is formed from a series of two-dimensional images (33) representing at least one physical property associated with the three-dimensional structure, such as a body organ having a lumen. A wire frame model of a selected region of interest is generated (38b). The wireframe model is then deformed or reshaped to more accurately represent the region of interest (40b). Vertices of the wire frame model may be grouped into regions having a characteristic indicating abnormal structure, such as a lesion. Finally, the deformed wire frame model may be rendered in an interactive three-dimensional display.

25 Claims, 12 Drawing Sheets

(56) References Cited

U.S. PATENT DOCUMENTS

| | | | |
|---|---|---|---|
| 4,367,216 A | 1/1983 | Mutzel et al. | |
| 4,391,280 A | 7/1983 | Miller | |
| 4,630,203 A | 12/1986 | Szirtes | |
| 4,668,915 A | 5/1987 | Daubin et al. | |
| 4,710,876 A | 12/1987 | Cline et al. | |
| 4,719,585 A | 1/1988 | Cline et al. | |
| 4,729,098 A | 3/1988 | Cline et al. | |
| 4,737,921 A | 4/1988 | Goldwasser et al. | |
| 4,751,643 A | 6/1988 | Lorensen et al. | |
| 4,791,567 A | 12/1988 | Cline et al. | |
| 4,821,213 A | 4/1989 | Cline et al. | |
| 4,823,129 A | 4/1989 | Nelson | |
| 4,831,528 A | 5/1989 | Crawford et al. | |
| 4,874,362 A | 10/1989 | Wiest et al. | |
| 4,879,668 A | 11/1989 | Cline et al. | |
| 4,958,932 A | 9/1990 | Kegelman et al. | |
| 4,984,157 A | 1/1991 | Cline et al. | |
| 4,985,834 A | 1/1991 | Cline et al. | |
| 4,985,856 A | 1/1991 | Kaufman et al. | |
| 4,993,415 A | 2/1991 | Long | |
| 5,006,109 A | 4/1991 | Douglas et al. | |
| 5,023,072 A | 6/1991 | Cheng | |
| 5,038,302 A | 8/1991 | Kaufman | |
| 5,047,772 A | 9/1991 | Ribner | |
| 5,056,020 A | 10/1991 | Feldman et al. | |
| 5,115,501 A | 5/1992 | Kerr | |
| 5,127,037 A | 6/1992 | Bynum | |
| 5,148,366 A | 9/1992 | Buchanan et al. | |
| 5,166,876 A | 11/1992 | Cline et al. | |
| 5,170,347 A | 12/1992 | Tuy et al. | |
| 5,187,658 A | 2/1993 | Cline et al. | |
| 5,204,625 A | 4/1993 | Cline et al. | |
| 5,229,935 A | 7/1993 | Yamagishi et al. | |
| 5,235,510 A | 8/1993 | Yamada | |
| 5,245,538 A | 9/1993 | Lis | |
| 5,261,404 A | 11/1993 | Mick et al. | |
| 5,265,012 A | 11/1993 | Amans et al. | |
| 5,267,155 A | 11/1993 | Buchanan | |
| 5,270,926 A | 12/1993 | Tam | |
| 5,283,837 A | 2/1994 | Wood | |
| 5,295,488 A | 3/1994 | Lloyd et al. | |
| 5,299,288 A | 3/1994 | Glassman et al. | |
| 5,313,567 A | 5/1994 | Civanlar et al. | |
| 5,322,070 A | 6/1994 | Goodman et al. | |
| 5,339,812 A | 8/1994 | Hardy | |
| 5,345,490 A | 9/1994 | Finnigan et al. | |
| 5,365,927 A | 11/1994 | Roemer et al. | |
| 5,412,563 A | 5/1995 | Cline et al. | |
| 5,412,763 A | 5/1995 | Knoplioch | |
| 5,437,278 A | 8/1995 | Wilk | |
| 5,452,416 A | 9/1995 | Hilton | |
| 5,458,111 A | 10/1995 | Coin | |
| 5,463,548 A | 10/1995 | Asada | |
| 5,506,984 A | 4/1996 | Miller | |
| 5,528,492 A | 6/1996 | Fukushima | |
| 5,542,003 A | 7/1996 | Wofford | |
| 5,581,460 A | 12/1996 | Kotake | |
| 5,581,671 A | 12/1996 | Gotto et al. | |
| 5,587,833 A | 12/1996 | Kamensky | |
| 5,611,025 A | 3/1997 | Lorensen et al. | |
| 5,623,586 A | 4/1997 | Hohne | |
| 5,630,034 A | 5/1997 | Oikawa et al. | |
| 5,666,400 A | 9/1997 | McAllister | |
| 5,704,367 A | 1/1998 | Ishikawa | |
| 5,715,449 A | 2/1998 | Peters, Jr. | |
| 5,740,267 A | 4/1998 | Echerer | |
| 5,742,291 A | 4/1998 | Palm | |
| 5,762,608 A | 6/1998 | Warne | |
| 5,779,634 A | 7/1998 | Ema | |
| 5,782,762 A * | 7/1998 | Vining | 600/407 |
| 5,793,969 A | 8/1998 | Kamentsky | |
| 5,807,256 A | 9/1998 | Taguchi et al. | |
| 5,825,908 A | 10/1998 | Pieper et al. | |
| 5,878,746 A | 3/1999 | Lemelson | |
| 5,891,030 A | 4/1999 | Johnson et al. | |
| 5,898,760 A | 4/1999 | Smets | |
| 5,898,793 A | 4/1999 | Karron | |
| 5,920,317 A | 7/1999 | McDonald | |
| 5,920,319 A * | 7/1999 | Vining et al. | 345/420 |
| 5,926,568 A * | 7/1999 | Chaney et al. | 382/217 |
| 5,957,138 A | 9/1999 | Lin et al. | |
| 5,971,767 A | 10/1999 | Kaufman et al. | |
| 5,986,662 A | 11/1999 | Argiro et al. | |
| 6,014,581 A | 1/2000 | Whayne | |
| 6,032,678 A | 3/2000 | Rottem | |
| 6,058,322 A | 5/2000 | Nishikawa | |
| 6,083,162 A * | 7/2000 | Vining | 600/407 |
| 6,117,073 A | 9/2000 | Jones | |
| 6,246,784 B1 | 6/2001 | Summers et al. | |
| 6,252,979 B1 | 6/2001 | Lee | |
| 6,272,366 B1 * | 8/2001 | Vining | 600/407 |
| 6,282,305 B1 | 8/2001 | Huo | |
| 6,292,577 B1 | 9/2001 | Takahashi | |
| 6,317,617 B1 | 11/2001 | Gilhuijs | |
| 6,366,683 B1 | 4/2002 | Langlotz | |
| 6,366,800 B1 | 4/2002 | Vining et al. | |
| 6,389,157 B2 | 5/2002 | Rogers et al. | |
| 6,415,048 B1 | 7/2002 | Schneider | |
| 6,490,370 B1 | 12/2002 | Krasinki | |
| 6,551,243 B2 | 4/2003 | Bocionek | |
| 6,630,937 B2 | 10/2003 | Kallergi | |
| 6,694,163 B1 | 2/2004 | Vining et al. | |
| 6,697,538 B1 * | 2/2004 | Angenent et al. | 382/285 |
| 6,766,043 B2 * | 7/2004 | Zeng et al. | 382/128 |
| 6,813,373 B1 | 11/2004 | Suri et al. | |
| 6,879,668 B2 | 4/2005 | Neuwald | |
| 6,909,913 B2 | 6/2005 | Vining | |
| 7,149,564 B2 | 12/2006 | Vining et al. | |
| 7,200,251 B2 * | 4/2007 | Joshi et al. | 382/128 |
| 7,289,651 B2 | 10/2007 | Vining et al. | |
| 7,792,565 B2 | 9/2010 | Vining | |
| 2001/0025279 A1 | 9/2001 | Krulak | |
| 2002/0004798 A1 | 1/2002 | Babula | |

FOREIGN PATENT DOCUMENTS

| | | | |
|---|---|---|---|
| AU | 757981 | 1/2002 | |
| CN | 1239253 | 12/1999 | |
| EP | 0231950 | 12/1987 | |
| EP | 0514587 | 11/1992 | |
| EP | 0961993 | 2/2005 | |
| GB | 2265775 | 10/1993 | |
| JP | 6103374 | 1/1986 | |
| JP | 03-176034 | 7/1991 | |
| JP | 05-130989 | 5/1993 | |
| JP | 05-189543 | 7/1993 | |
| JP | 05-324840 | 12/1993 | |
| JP | 06-020065 | 1/1994 | |
| JP | 06-028455 | 2/1994 | |
| JP | 06-068235 | 3/1994 | |
| JP | 06-176130 | 6/1994 | |
| JP | 3184327 | 4/2001 | |
| WO | 9114397 | 10/1991 | |
| WO | 9424640 | 10/1994 | |
| WO | 9520270 | 7/1995 | |
| WO | 9613207 | 5/1996 | |
| WO | WO 9613207 A1 * | 5/1996 | A61B 5/00 |
| WO | 9816903 | 4/1998 | |
| WO | 99/66394 | 12/1999 | |
| WO | 03046810 | 6/2003 | |

OTHER PUBLICATIONS

Geiger, B., et al., "Simulation of Endoscopy", Joint Conference, Computer Vision, Virtual Reality and Robotics in Medicine and Medical Robotics and Computer-Assisted Surgery Proceedings, Apr. 1995, pp. 277-281.

European Partial Supplementary Search Report dated Aug. 24, 2007.

Gonzalez, R., et al., "Digital Image Processing", 8.4 Morphology, 1992, pp. 518-521.

"The ACR Breast Imaging Reporting and Data System (BI-RADS®)", Copyright © 1994-2002 American College of Radiology, Revised Jun. 1, 2000.-

(56) References Cited

OTHER PUBLICATIONS

Bell, D.S.., et al., "Evaluation of UltraSTAR: Performance of a Collaborative Structured Data Entry System", 1994, AMIA, Inc.; Symposium Supplement, pp. 216-222.

T.L. Schulley, et al. "A High Resolution Nonlinearity Correcting A/D Converter Archiecture," Jun. 3-6, 1993, pp. 1212-1215, 1993 IEEE International Symposium on Circuits and Sytems.

Vining, D.J., Padhabi, A.R., Wood, S., Zerhouni, E.A., Fishman, E.K., and Kuhlman, J.E., "Virtual Bronchoscopy: A New Perspective for Viewing the Trachebronchial Tree." Radiology. Nov. 1993, vol. 189 (P).

Watt, Alan. "3D Computer Graphics." 2nd Edition, Addison-Wesley Pub Co., 1993, pp. 320-323.

Strong, et al., "Applications of Three-Dimensional Display Techniques in Medical Imaging," J. Biomed Eng. 1990, vol. 12, May, pp. 233-238.

General Electric Medical Systems, "3D Navigator for CT or MR Advanced Visualization Software", 1996.

Picker International VoyagerTM Product Data, "VoyagerTM Visualization Tools for the Q-Series Scanner", 1997.

Bidgood, W. Dean, Jr., "Clinical Importance of the DICOM Structured Reporting Standard", International Journal of Cardiac Imaging 14: 307-315, 1998.

Bidgood, W. Dean, Jr., "Documenting the Information Content of Images". Proc AMIA Annu Fall Symp (1997), pp. 424-428.

Campbell, K.E., et al., "A Computer-Based Tool for Generation of Progress Notes", 1993; Symposium Supplement 284-288.

Chronaki, C. et al., "I2Cnet Medical Image Annotation Service", Medical Informatics, Online! vol. 22, No. 4, 1997, pp. 337-347.

Dockray, Karl T., "Solo Practice Management: Value of a Computerized Reporting System", Computers in Radiology, JR 1994, 162:1439-1441.

eDict Systems, Inc., www.edictation.com printer webside on Nov. 21, 2000.

Friedman, C., et al., "A Schema for Representing Medical Language Applied to Clinical Radiology", Journal of the American Medical Informatics Assoc., vol. 1, No. 3, May/Jun. 1994, 1:233-248.

Hundt, W., et al., "A Computer-based reporting system in radiology of the chest", European Radiology, 8, 1002-1008 (1998), Springer-Verlag 1998, 8:1002-1008.

Langlotz, Gp.P., MD, PhD, "A Graphical Speech-guided Structured Reporting System", 1999 Scientific Program Radiological Society of North America 56th Scientific Assembly and Annual Meeting, Supplement Nov. 1999, v213(p), p578.

Poon, A.D., et al., "PEN-Ivory, The Design and Evaluation of a Pen-Based Computer System for Structured Data Entry", Stanford University School of Medicine, Journal of the American Medical Informatics Assoc., 1994; (Symposium Supplement) 447-451.

Puerta, A., et al., "Towards a General Computational Framework for Model-Based Interface Development Systems", Stanford University, Proceeding of the International Conference on Intelligent User Interface Design, Calif. 1999.

Vining, et al., "Freeflight", Digestive Disease Week and the 100th Annual Meeting of the Gastroenterological Assoc., May 16-19, 1999, Orlando, FL, program v116, n4, p2.

Vining, et al., "New Paradigm for Virtual Colonoscopy Processing and Reporting", and "New Paradigm for Digital Image Reporting", 1999 Scientific Program Radiological Society of North America 85th Scientific Assembly and Annual Meeting, Supplement Nov. 1999, v213(p), p577 and 579.

Chen, et al., "A Distributed and Interactive Three Dimensional Medical Imaging System", Computer Med Imaging Graph, Sep.-Oct. 1994; 18(5):325-37*.

Wiegand, et al., "The Surgical Workstation: Surgical Planning using Generic Software", Otolaryngol Head Neck Surg, Sep. 1993; 1093 (3 Pt 1): 434-40*.

Shapiro, et al., "Preliminary Results of a Modified Surface Rendering Technique in the Display of MR Angiography Images", Magn Reson Imaging, 1994;12(3):461-8*.

Rusinek, et al., "Volumetric Rendering of MR Images", Radiology Apr. 1989;17(1):269-72.*.

Amended Answer and Counterclaim of Defendant Voxar Limited, Filed Oct. 10, 2002.

Shinagawa, Y., et al., "Automating View Function Generation for Walk-through Animation Using a Reeb Graph", Proceedings Computer Animation '90, at pp. 227-237 (Springer-Verlag 1990).

Nomura, et al., "Walking through a Human Ear", Act Otolaryogol at 107:366-370 (1989).

Mani, et al., "A Computer-Assisted Radiologic Reporting System", Radiology 108:587-596, Sep. 1973.

Wheeler, et al., "The John Hopkins Radiology Reporting System", Radiology 119:315-319, May 1976.

Bluemke, et al., "An Automated Radiology Reporting System That Uses HyperCard", Computers in Radiology, AJR 1993; 160:185-187 0361-803X/93/1601-0185 American Roentgen Ray Society, Jul. 23, 1992.

Pendergrass, et al., "An On-Line Computer Facility for Systematized Input of Radiology Reports". Radiology. Mar. 1969;92(4):709-13.

Barnhard, et al., "Computer Autocoding, Selecting and Correlating of Radiologic Diagnostic Cases" American Journal of Roentgenology, vol. 96, 854-863, 1966.

Bell, et al., "Experiments in Concept Modeling for Radiographic Image Reports", J Am Med Informatics Assoc. May-Jun. 1994; 1(3):249-62.

Kahn, Jr., et al., "Structed Entry of Radiology Reports Using World Wide Web Technology", RadioGraphics 1996; 16:683-691, RSNA, 1996.

Brolin, "MEDELA: An Electronic Data-Processing System for Radiological Reporting", Radiology 103:249-255, May 1972.

Leeming, et al., "Advances in Radiologic Reporting with Computerized Language Information Processing", Radiology 133:349-353, Nov. 1979.

Dietrich, "Knowledge-Based Computer-Assisted Diagnosis of Chest Radiographs", Radiologic Clinics of North America—vol. XVI, No. 3, Dec. 1978.

Jost, "Radiology Reporting", Radiologic Clinics of North America—vol. 24, No. 1, Mar. 1986.

Langlotz, "Enhancing the Expressiveness of Structured Reporting Systems", Journal of Digital Imaging, vol. 13, No. 2, Suppl. 1 (May), 2000: pp. 49-53.

Du-Yih Tsai, et al., "Computer-based Measurement of Right and Left Ventricular Volumes in Magnetic Resonance Imaging", IMTC/94, Advanced Technologies in I & M, 1994 IEEE Hamamatsu, Japan May 10-12, 1994, New York, NY, USA IEEE, May 10, 1994, pp. 971-974, XP010121821.

Lorensen, et al., "Marching Cubes: A High Resolution 3D Surface Construction Algorithm", Siam Journal on Computing, Society for Industrial and Applied Mathematics, US, vol. 21, No. 4, Jul. 1, 1987, pp. 163-169, XP000576999.

Rubin, et al., "Perspective Volume Rendering of CT and MR Images: Applications for Endoscopic Imaging", Radiology, Oak Brook, IL, US, vol. 199, No. 2, May 1, 1996, pp. 321-330, XP002083446.

Cavaye, et al., "A New Technique for Intraluminal Hollow Organ Imaging: Three-Dimensional Ultrasound", Journal of Laparoendoscopic Surgery, vol. 1, No. 5, 1991, Mary Ann Liebert, Inc., Publishers. Kobayashi, et al., "Endoscopic Visualisation of Luminal Organs and Great Vessels with a Three-Dimensional CT Scanner: A New Trial using Volumetric CT", Nippon Acta Radiologica, vol. 52, No. 8, pp. 1195-1197 (1992).

Robb, et al., "A Software System for Interactive and Quantitative Visualization of Multidimensional Biomedical Images", Australasian Physical & Engineering Sciences in Medicine (1991), vol. 14, No. 1.

Sahoo, P.K., "A Survey of Thresholding Techniques," Computer, Vision, Graphics, and Image Processing (1988), No. 2, Duluth, MN, USA, pp. 233-260.

* cited by examiner

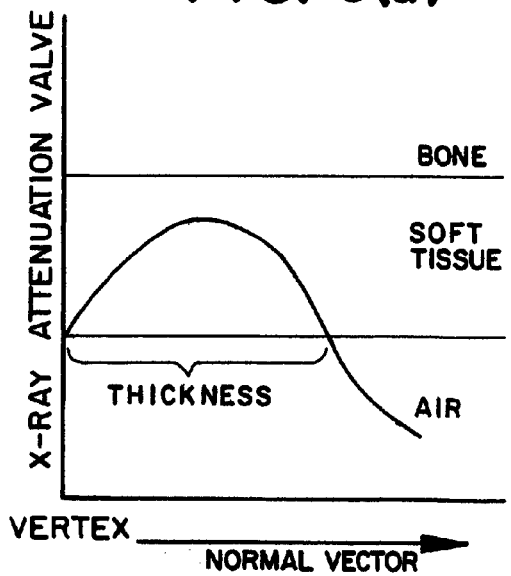
FIG. 6(a)
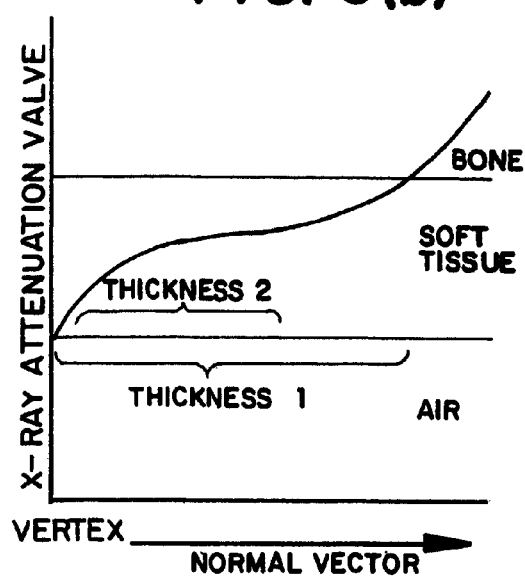
FIG. 6(b)
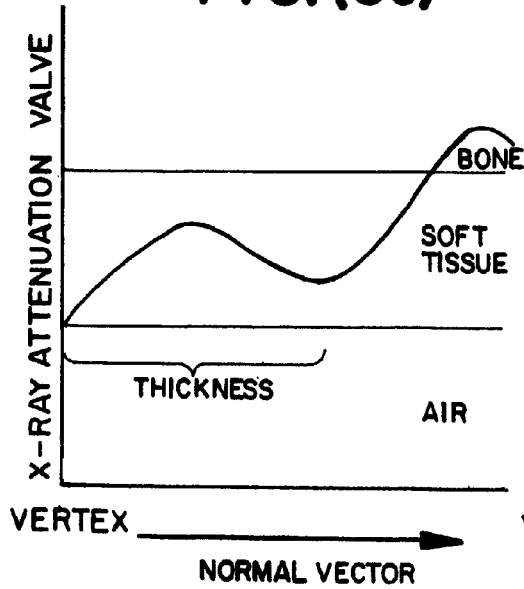
FIG.(6c)
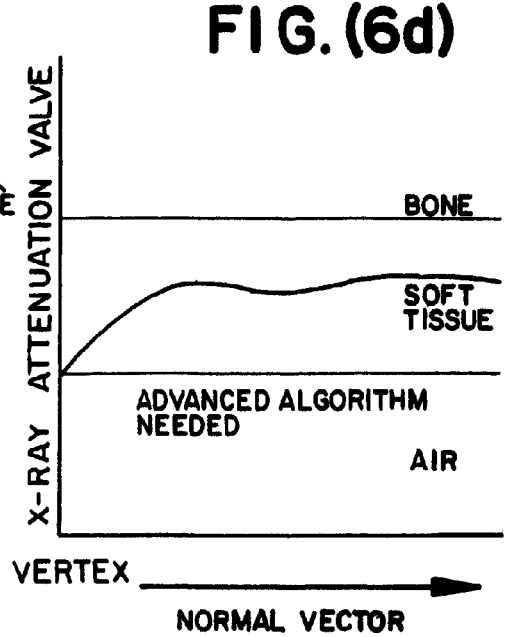
FIG.(6d)

VIRTUAL ENDOSCOPY WITH IMPROVED IMAGE SEGMENTATION AND LESION DETECTION

This application is a continuation application of U.S. patent application Ser. No. 09/856,683, filed on Aug. 23, 2001, which is a §371 application of PCT/US99/28030, filed on Nov. 24, 1999, which claims priority to U.S. Provisional Application No. 60/109,966, filed on Nov. 25, 1998. This application also claims the benefit of and is a continuation in part of U.S. patent application Ser. No. 09/299,061, filed on Apr. 23, 1999, now U.S. Pat. No. 6,366,800, which is a continuation of U.S. patent application Ser. No. 08/805,584, filed on Feb. 24, 1997, now U.S. Pat. No. 5,920,319. The entire disclosure of each of the foregoing applications is incorporated by reference herein.

FIELD OF THE INVENTION

The present invention relates to a system and method for interactively displaying a three-dimensional rendering of a structure and, more particularly, to a system and method for automatically analyzing such structures for potential abnormalities.

BACKGROUND OF THE INVENTION

For many forms of cancer, early detection is essential for a favorable prognosis. A cancerous growth must be detected at an early stage before the cancer is allowed to grow and spread. This is particularly true for colorectal and lung cancers. As a result, endoscopic techniques have been developed to examine the colon and tracheobronchial airways for the growth of precancerous and cancerous masses.

Regarding colorectal cancer, the American Cancer Society and the National Cancer Institute recommend routine screening in order to provide a means for early detection of abnormal growths. Under those guidelines over 50 million Americans should undergo annual colorectal screening. However, only a small percentage of the population undergoes colonoscopy screening each year. The underutilization of such screening exists, at least in part, because conventional colonoscopies require a patient to be sedated so that a flexible endoscope can be inserted into the patient's anus. Another problem is that conventional colonoscopies fail to provide access to the entire colon in approximately 15% of cases. Colonoscopies also expose patients to the risk of bowel perforation. Accordingly, it is understandable that patients are reluctant to undergo, or repeatedly subject themselves to, such an invasive procedure.

Consequently, virtual endoscopic techniques have been, and are continuing to be developed. Virtual endoscopy that utilizes computer reformation of radiologic cross-sectional images is a minimally invasive alternative to conventional fiberoptic endoscopy. Virtual endoscopy reduces the risk of perforation, does not require any sedation, and is considerably less expensive than the fiberoptic endoscopy method. For example, virtual colonoscopy techniques generally require bowel cleansing, gas distension of the colon, a 10-60 second helical computed tomography (CT) scan of a patient's abdomen and pelvis, and human visual analysis of multiplanar two-dimensional (2D) and three-dimensional (3D) images created from CT data.

Although virtual colonoscopy techniques provide excellent images of the colon in three-dimensions, a correct diagnosis relies upon a physician's ability to properly identify small (approximately 3-10 mm), and sometimes subtle, masses within hundreds of multiplanar two-dimensional and three-dimensional images. Such human inspection is time consuming, tedious, expensive, and under certain circumstances prone to error of interpretation. Accordingly, it would be highly beneficial to provide an automatic virtual endoscopic system and method for automatically analyzing and/or detecting abnormalities, such as abnormal growths, in a targeted structure or organ system, such as the walls of a colon or trachea.

SUMMARY OF THE INVENTION

In accordance with the present invention, a computer-implemented method and computer system are provided for interactively displaying a three-dimensional rendering of a structure, generally having a lumen. In a specific application, the method may be utilized for analyzing regions having certain characteristics of wall structure, such as thickness or shape, to detect, for example, abnormal masses. In accordance with the method of the present invention, a three-dimensional volume of data is formed from a series of two-dimensional images representing at least one physical property associated with the three-dimensional object. A surface of a selected region of interest, optionally an isosurface, is created in the computer from the volume of data based on selected values of the physical properties representing the selected region of interest. A wireframe model of the surface is generated by the computer. The wireframe model may be purposefully deformed by the computer to more accurately match the object of interest. The wireframe model is analyzed to detect, by computer, those sections of the object having the selected characteristic such as abnormal wall structure. For example, the wireframe model includes a plurality of vertices. The computer-implemented method groups the vertices of the wireframe model into populations having a characteristic indicating abnormal wall structure. The wireframe model with highlighted abnormal portions is then rendered by the computer into an interactive three-dimensional display on the computer monitor. Alternatively, the locations of selected abnormal portions may be stored and indexed in the computer without necessity of an interactive display.

In specific applications, a system for interactively displaying three-dimensional structures is provided. Volume formation means is included for forming a three-dimensional volume of data from a series of two-dimensional images representing at least one physical property associated with a three-dimensional body. A wireframe modeling means is provided for producing a wireframe model of a selected region or object of interest. A wireframe deforming means is provided for deforming the wireframe model to more accurately represent the object of interest. Finally, rendering means may optionally be provided for rendering the wireframe model in an interactive three-dimensional display, therein producing a virtual three-dimensional environment.

In a specific embodiment, segmentation means may be provided for segmenting the object of interest from the volume of data based on selected values of the physical property representing the region of interest. In addition, the modeling means may function to produce the wireframe model from the segmented region of interest.

The wireframe model may be produced to include a plurality of vertices, with each vertex having a coordinate position. In such an embodiment, the deforming means may include refinement means for refining the wireframe model by adjusting the coordinate positions of the vertices to more accurately represent the object of interest.

As a further option, the vertices of the wireframe model may be grouped into regions having a characteristic indicating abnormal structure. The regions of abnormal structure may then be analyzed to identify regions having a high degree of abnormality. The abnormal structure can be designated and indexed by the computer either as a comprehensive listing or as a listing dependent on the degree of abnormality.

The system may also include provision for targeting abnormalities and for determining the position of a biopsy needle within the three-dimensional virtual environment. In such an embodiment, an interactive three-dimensional display of a rendered wireframe model of a selected object of interest is displayed from the perspective indicating the position of the biopsy needle within the three-dimensional virtual environment.

BRIEF DESCRIPTION OF THE DRAWINGS

The foregoing summary, as well as the following detailed description of the preferred embodiments of the present invention, will be better understood when read in conjunction with the accompanying drawings, in which:

FIGS. 6 a-d are diagrams illustrating methods of calculating wall thickness at a vertex of a wireframe model by analyzing the intensity profile along the normal vector originated at the vertex;

FIG. 15 is a schematic representation of section of two-dimensional image data containing hypothetical soft tissue/opacified stool and opacified stool/air interfaces;

FIG. 16 is a schematic representation of simplified section of two-dimensional image data containing soft tissue/opacified stool and opacified stool/air interfaces; and FIG. 17 is a schematic representation of the section of two-dimensional image data of FIG. 16 showing edge gradient effects resulting from a simple digital subtraction scheme.

DETAILED DESCRIPTION OF THE PREFERRED EMBODIMENTS

Figure 1:
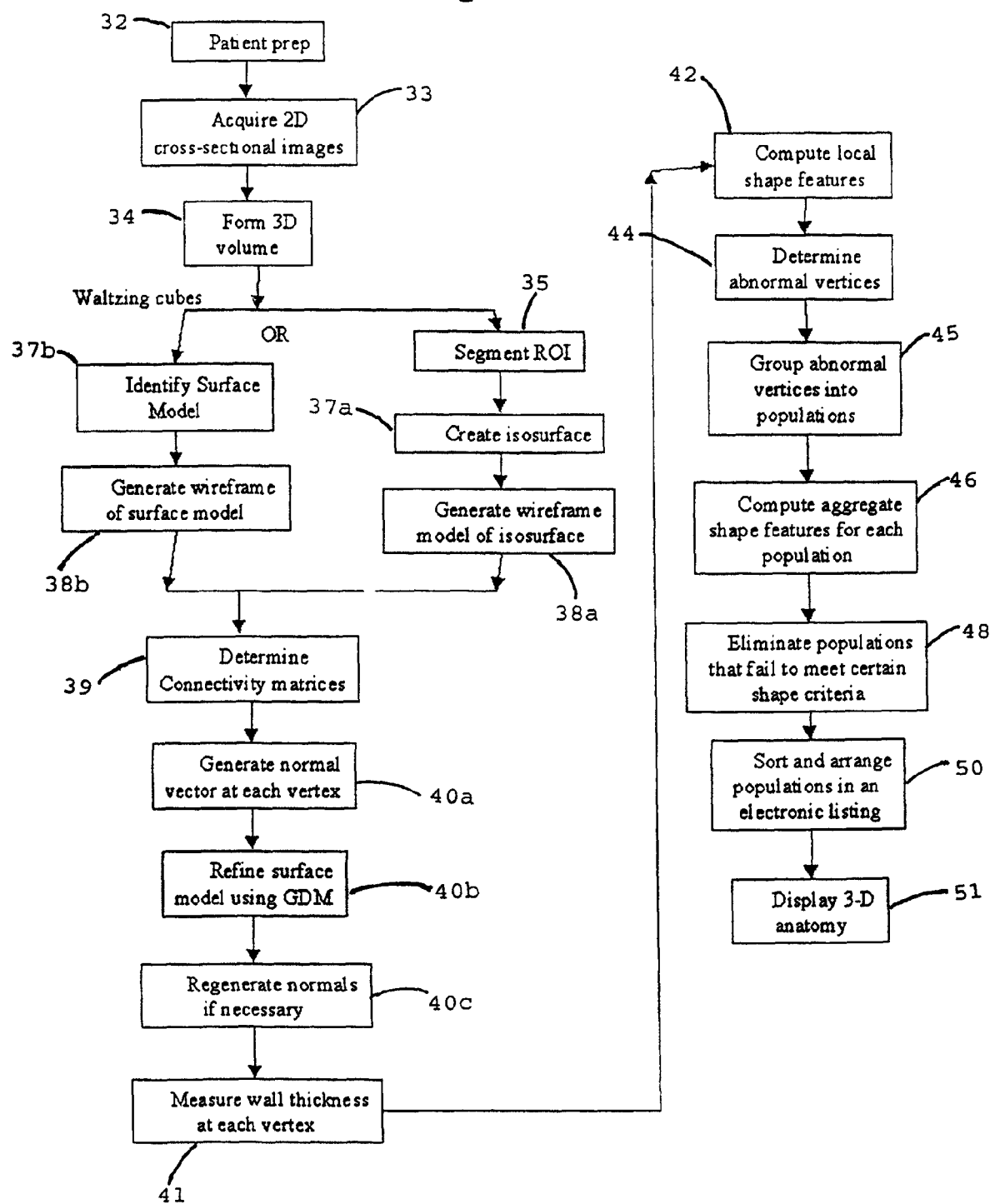
FIG. 1 is a flowchart representing a method in accordance with the present invention of producing an interactive, three-dimensional rendering of a selected organ system, such as an organ containing a lumen, and of detecting potentially abnormal areas of the organ system.
Figure 2:
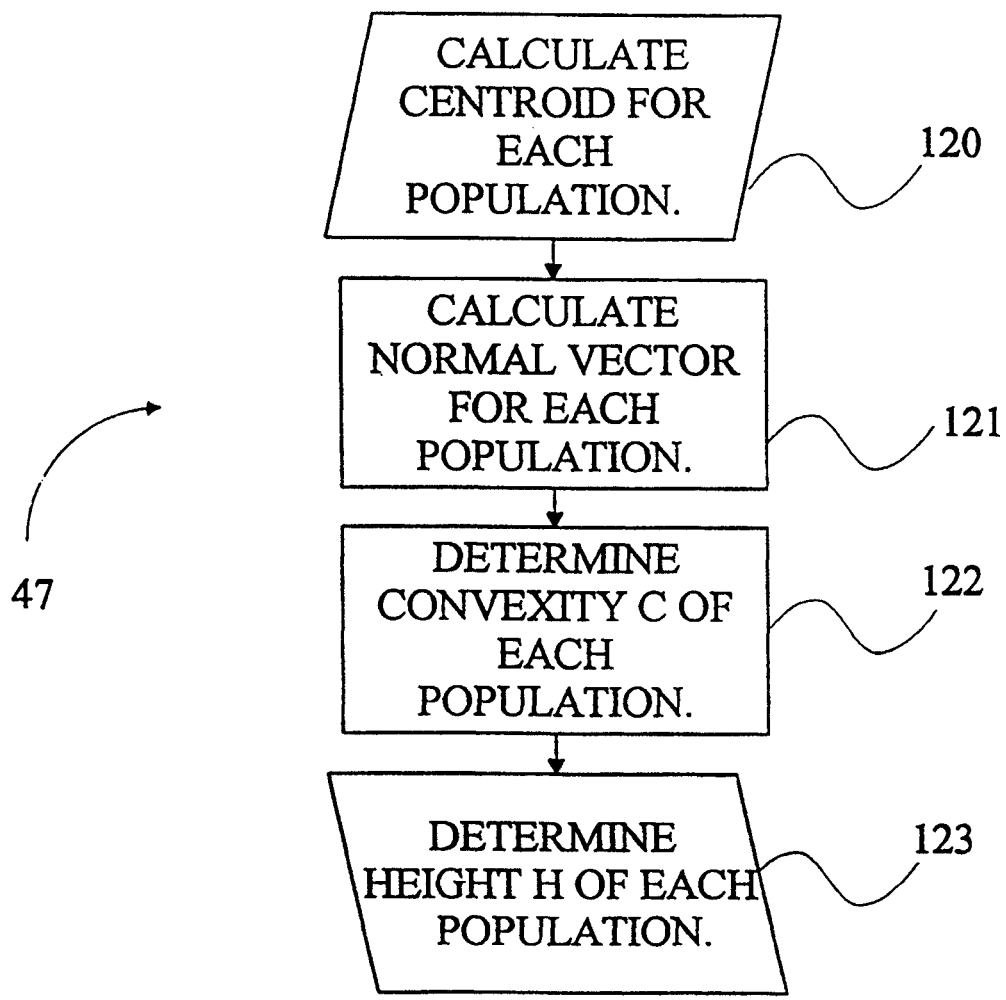
FIG. 2 is a flowchart representing a method for analyzing the shape of a population representing a potentially abnormal area within the selected organ system.
Figure 4:
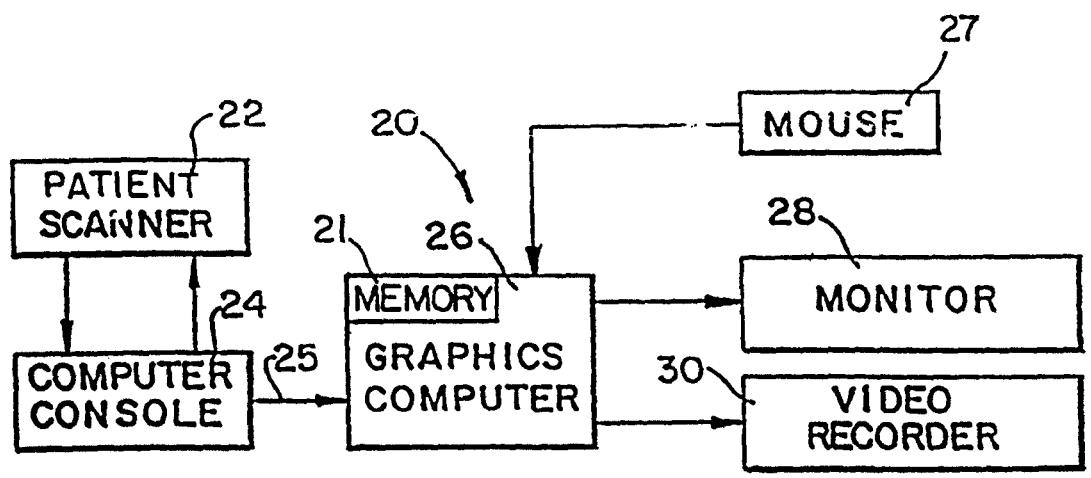
FIG. 4 is a block diagram of a system used in the method of the present invention.

The present invention generally relates to a computer-implemented method and system, as schematically represented in FIGS. 1, 2, and 4 for generating interactive, three-dimensional renderings of three-dimensional structures generally having a lumen. The structures are usually in the general form of selected regions of a body and in particular, human or animal body organs which have hollow lumens such as colons, blood vessels, and airways. In accordance with the present invention, the interactive three-dimensional renderings are generated in a computer-controlled process from a series of two-dimensional, cross-sectional images of the selected body organ acquired, for example, from a helical computed tomography (CT) scan. The three-dimensional renderings are interactive in that such renderings can be manipulated by a user on a visual display of a computer system, such as a computer monitor, to enable movement in, around and through the three-dimensional structure, or slices or cuts of such three-dimensional structure, while simultaneously displaying multiplanar views centered on a point that changes in response to the movement, or on a point selected by the user.

The computer-generated interactive three-dimensional renderings can be constructed from surface renderings of the organ system or from volume renderings of the organ system and surrounding anatomy and may be presented from surface and volume renderings simultaneously in the same three-dimensional display window. In a selected embodiment, a surface rendering of an organ can be incorporated into a volume rendering of the surrounding anatomy using texture memory in order to achieve a combined surface/volume rendering, or a hybrid rendering effect, wherein the surface rendered organ may be highlighted in the context of the volume-rendered surrounding anatomy. In yet another embodiment, multiplanar views such as orthogonal (sagittal, coronal, and axial) or oblique views, may be presented simultaneously with a surface-rendered organ and surrounding volume-rendered anatomy in either separate three-dimensional display windows or in a combined single three-dimensional display or window.

A computer-controlled system 20 in accordance with the present invention is shown schematically in FIG. 4. The system 20 is generally as described in U.S. Pat. No. 5,782,762, which is incorporated herein by reference. Briefly, a computer console 24 is used to operate a scanner 22 to produce a series of two-dimensional, cross-sectional images of a selected three-dimensional object. The two-dimensional images are transferred from the console 24 to a computer graphics workstation 26 over a computer network 25. The graphics computer 26 is used to generate a three-dimensional rendering, such as a three dimensional surface rendering, of the selected object and to automatically identify potentially abnormal regions of the structure. The three-dimensional rendering is displayed on a computer monitor 28. Additionally, the displayed rendering can be recorded on a video recorder 30 or photographed and/or digitally recorded for future viewing. Various inputs, such as a computer mouse 27, are provided to the graphics computer to permit a user to manipulate the displayed imagery.

The scanner 22 can be a General Electric HiSpeed Advantage Helical CT Scanner (GE Medical Systems, Milwaukee, Wis.). For scanning a patient's lungs, the scanner is typically operated with an X-ray beam collimation of 3 mm, a pitch of 1:1, a 1 mm reconstruction interval, a display field-of-view of 25.6 cm, and a 512×512 matrix. For scanning a patient's colon, the scanner is typically operated with a beam collimation of 5 mm, a pitch of 2:1, a 1 mm reconstruction interval, a display field-of-view of 40 cm, and a 512×512 matrix. These protocols typically result in approximately 200 thoracic CT images or 500 abdominal CT images, which occupy approximately 100 MB and 250 MB of disk storage space, respectively. However, the protocols can be modified to optimally acquire image data of specific organ systems, or to adapt to advances in scanner technology. Alternatively, MR scanning can be employed, or any future technology that generates image data.

The image data can be stored in any of a variety of image formats. For example, the image data can be stored using the digital imaging and communications in medicine (DICOM) standard, or as raw binary slices, or in a variety of volume formats. For example, the image data can be stored in the computer memory in an internal data format which allows the image files to be saved as a single data volume instead of individual image files. The internal data format can also permit standard compression and uncompression techniques to be incorporated, thereby reducing computer disk storage requirements.

Figure 11:
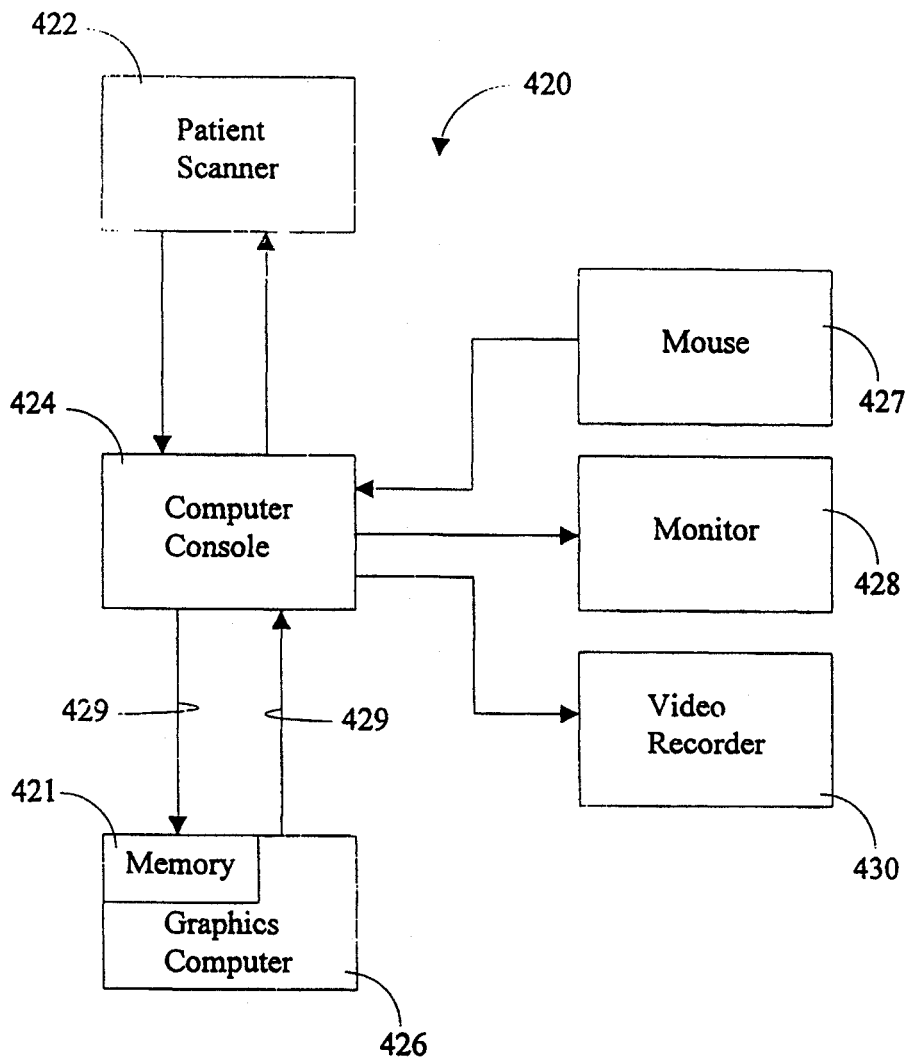
FIG. 11 is a block diagram of an alternate embodiment of the system used in the method of the present invention.

An alternate arrangement of the system in accordance with the present invention is shown schematically in FIG. 11. The system of FIG. 11 is particularly well suited for use with a centralized high-speed graphics computer. The scanner 422, computer console 424, graphics computer 426, memory 412, mouse 427, monitor 428, and video recorder 430 are essentially the same as the corresponding components of system 20. However, in system 420, the mouse 427, monitor 428, and video recorder 430 are connected to computer console 424. Additionally, the graphics computer 426 is connected to the computer console 424 via a computer network 429 such as an outside network permitting remote connection of the graphics computer. The computer network 429 enables the graphics computer 426 to both receive image data from the computer console 424 and transmit the results of subsequent image data analysis to the computer console 424. Accordingly, the graphics computer 426 can be located remotely from computer console 424. Further, graphics computer 426 can be used to analyze image data received from more than one computer console.

A method for generating interactive, three-dimensional renderings of a selected structure having a lumen and indicating potentially abnormal regions of the structure in accordance with the present invention is generally set forth in FIG. 1. The method can be implemented by computer. The steps of patient preparation 32, acquisition of two-dimensional images 33, formation of a three-dimensional volume 34, segmentation of a region of interest 35, creation of an isosurface of the region of interest 37a, and generation of a wireframe model of the isosurface 38a may be effected in the general manner described in U.S. Pat. No. 5,782,762, which is incorporated herein by reference or any comparable methodologies and algorithms. Alternatively, instead of generating a wireframe model from an isosurface of a segmented region of interest pursuant to steps 35, 37a and 38a, the wireframe model can be generated at step 38b after a surface model is identified at step 37b from the three-dimensional volume formed at step 34.

Patient preparation 32 will be dictated by the organ system to be examined. For example, if the patient's colon is to be examined, the patient is prepared using bowel cleansing and insufflation with gas to distend the colon. In one embodiment, a hand-operated air bulb may be used to distend the colon. The colon is inflated via a rectal catheter by squeezing the air bulb to instill puffs of room air into the colon.

Alternatively, the colon may be inflated with carbon dioxide ($CO_2$) or other gas, such as nitric oxide (NO), which exhibits a high lipid solubility and a high partial pressure gradient across the colonic mucosa. The combination of properties provided by carbon dioxide results in less uncomfortable abdominal symptoms for the patient following an examination. However, the high lipid solubility and high partial pressure gradient across the mucosa mean that the carbon dioxide is quickly absorbed by the patient. Therefore, the pressure of carbon dioxide within the colon must be continually monitored and maintained at a beneficial level during the course of an examination. Toward that end, an electronic carbon dioxide insufflator, such as those currently used for laparoscopic surgery procedures, is preferably used to instill the carbon dioxide at a constant flow rate (e.g., 1-15 liters/min) until a preset pressure (e.g., 0.04 atm) is obtained. The insufflator then maintains a constant pressure during the course of the examination.

The patient may be placed on a low-residue diet for a 24 hour period preceding the collection of image data. In addition, the patient can be given an oral contrast agent (barium-containing or iodine-containing mixture) to become incorporated in the fecal content to readily distinguish the stool from surrounding soft tissue structures, including the colon wall. The contrast agent may be used in conjunction with a cathartic agent to rid the bowel of the bulk of stool. The opacified stool may then be digitally removed from the CT image data in order to render an unimpeded colon. Without adequate bowel cleansing or the use of an oral contrast agent, stool and normal colon wall or colon lesions may be indistinguishable in computed tomography or other imaging modalities. For example, the contrast agent may comprise a barium-containing mixture or an iodine-containing compound for opacifying solid or liquid stool. In the case of rendering a patient's airways, the patient can be administered a bolus of non-ionic intravenous iodinated contrast agent to aid in distinguishing blood vessels from surrounding airways.

Once the patient has been prepared, two dimensional, cross-sectional images of the selected structure are acquired at step 33 with the use of a scanner 422, such as a helical computed tomography (CT) scanner or magnetic resonance imaging (MRI) scanner. The two-dimensional images are arranged in computer memory 421 (i.e., random access memory (RAM)) to create a three-dimensional data volume at step 34. To create isocubic volume elements (i.e., voxels), an interpolation method, including but not limited to trilinear interpolation, may be applied.

At step 35, a region of interest is segmented from the three-dimensional data volume. The purpose of segmentation is to isolate a region of interest within the three-dimensional data volume prior to three-dimensional rendering. In general, medical image segmentation is complicated by image noise, partial volume effects, and the fact that similar intensity values are shared by different anatomical structures. However, when a thin-walled soft tissue structure encompasses a gas-filled lumen, segmentation of that structure can be effectuated by selecting the gas column as the region of interest. The gas column can be effectively segmented because the boundary between gas and soft tissue is relatively distinct and sharp. Further, the outside surface of the gas column corresponds to the inside surface of the organ of interest. Similarly, when a thin-walled soft tissue structure encompasses a contrast enhanced blood-filled lumen, segmentation of that structure can be effectuated by selecting the contrast-enhanced blood column as the region of interest. Accordingly, a simple thresholding or region growing technique, along with a morphological dilation away from air or blood vessel and towards soft tissue, can be utilized for segmentation purposes.

However, in order to refine and to improve the accuracy of the segmentation process, especially as selected structures have varying characteristics (e.g., changing diameter, wall thickness, and/or X-ray attenuation values), more sophisticated segmentation procedures can be employed. One such procedure adaptively adjusts the threshold value defining the region of interest to more accurately segment specific sections of the organ during a region growing process as described in U.S. Pat. No. 5,920,319 incorporated herein by reference. Alternatively, the accuracy of segmentation can be improved by refining (or deforming) the wireframe model generated in steps 38a and 38b of FIG. 1 using a geometric deformable model (GDM) at step 40b.

Figures 15, 16, 17:
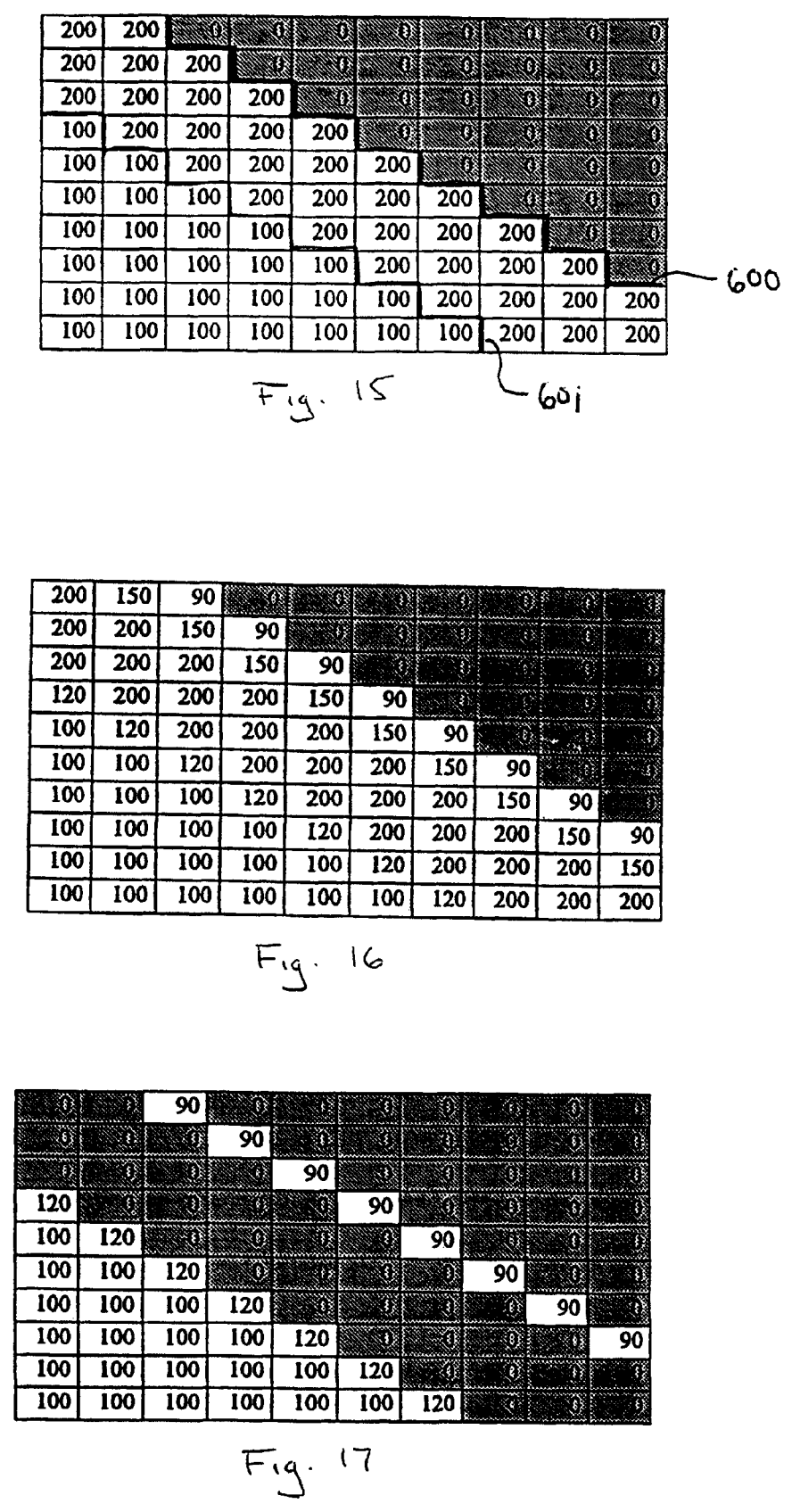

Referring again to FIG. 1, when a patient's colon is to be rendered and a contrast agent has been used to opacify stool and/or residual water, the segmentation step 35 includes the step of digitally removing the opacified stool/water from the CT image data in order to render an unimpeded colon. Digital removal of opacified feces is difficult due to the fact that simple digital subtraction leaves behind edge gradients. The appearance of edge gradients is illustrated in FIGS. 15-17. FIG. 15 is a schematic representation of a section of image data representing hypothetical CT image data showing the measured X-ray attenuation values associated with a two dimensional array of voxels. Soft tissue is represented by a value of 100, opacified stool by a value of 200, and air by a value of 0. In this simplified model, actual interfaces between different species is presumed to lie on the boundary between adjacent voxels. Accordingly, an interface 600 between soft tissue and opacified stool appears as the boundary between the voxels having a value of 100 and those having a value of 200. Similarly, an interface 601 between opacified stool and air appears as the boundary between the voxels having a value of 200 and those having a value of 0.

In reality however, sections of actual interfaces are likely to fall within certain voxels. The X-ray attenuation values measured for those voxels will be an average of the X-ray attenuations for the different species comprising the interface. Such volume averaging effects blur the interfaces. As illustrated in FIG. 16, the actual soft tissue/opacified stool boundary falls somewhere within the voxels having a measured value between 100 and 200. Likewise, the actual opacified stool/air interface lies somewhere within the voxels having a measured value between 200 and 0.

The effect of a simple digital removal scheme, whereby all values that are 150 or greater are set to zero, on the section illustrated in FIG. 16 is shown in FIG. 17. It is readily apparent that a ridge of voxels having a measured value of 90 is left behind and, therefore, will incorrectly be considered part of the soft tissue. In addition, although the true soft tissue/opacified stool interface lies somewhere within the voxels having a value of 120, the removal scheme automatically assumes that all of those voxels belong to the soft tissue. It will of course be appreciated that the edge effects encountered in real image data will be even more complex, due at least in part to inherent fluctuations in the measured values.

In view of the foregoing, when opacified stool is to be subtracted from the image data, an adaptive thresholding technique (as previously described in U.S. Pat. No. 5,920, 319) and/or a geometrically deformable model approach can be used to model both the gas column and the adjacent stool. These 3D models can then be analyzed separately, or merged to create a contiguous colon model. For example, the geometric deformable models initialized separately in the gas column and adjacent stool can be allowed to evolve until the boundaries of the two models merge.

Returning to FIG. 1, once the region of interest has been segmented at step 35, an isosurface of the region of interest is created at step 37a. The isosurface can be generated using a variant of a marching cubes algorithm. The isosurface is used to generate a wireframe model at step 38a. The wireframe model comprises a polygonal mesh that corresponds to the surface of the region of interest. Specifically, a plurality of vertices, each vertex having a coordinate position, are interconnected to produce the wireframe model.

Figure 12:
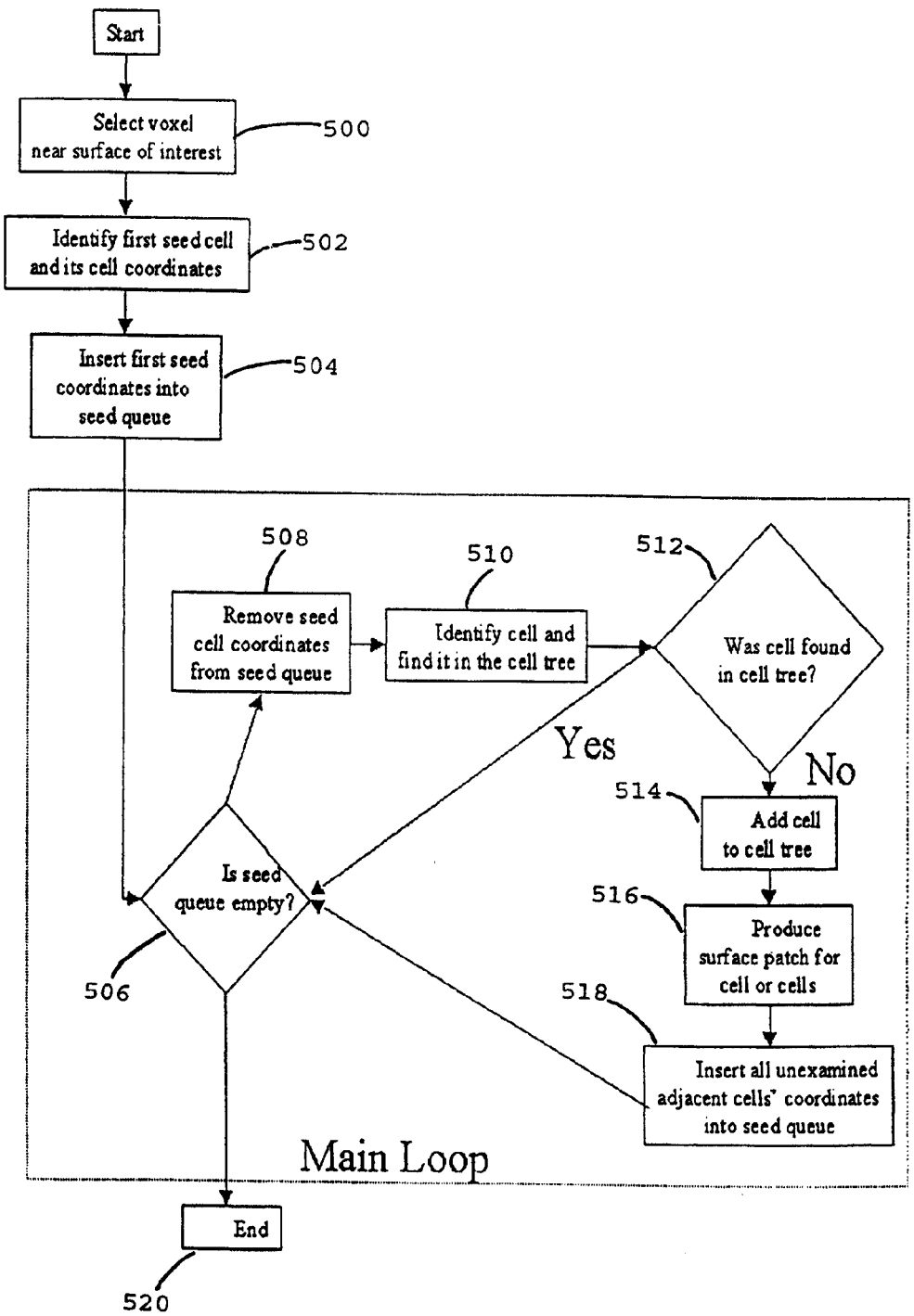
FIG. 12 is a flowchart representing a method for creating a selected surface of a region of interest.

Alternatively, a waltzing cubes algorithm can be employed as shown in FIG. 12 to first identify a surface model at step 37b and then to generate a wireframe of the surface model at step 38b without the help of initial segmentation 35. The generated surface can be an isosurface, such as that produced by a marching cubes variant, or it can be a variable-thresholded surface.

First, a voxel near the surface of interest within the volume of data is selected at step 500. This selection can be automated or explicitly identified by the user. Using this selected voxel, the first seed cell and its coordinate are identified at step 502. A cell is defined as the junction of eight adjacent image voxels, four in an upper image plane and four in a lower image plane, such that the eight voxels form a 2×2×2 cubic cell. A cell coordinate defines its exact location within the volume of data. The first seed cell is defined as any cell near the selected voxel that produces a surface patch belonging to the surface of interest. The first seed cell can be determined by iteratively examining all cells within an increasing radius centered on the selected voxel. Visually, each successive iteration examines all cells that lie on the surface of a sphere centered on the selected voxel as the radius is increased, until the nearest surface patch producing cell is identified. This method is accurate but computationally slow. Alternatively, cells that lie along each direction of each coordinate axis (i.e. −X, X, −Y, Y, −Z, Z) centered on the selected voxel can be examined until the nearest seed cell is identified. This method is fast but requires a more exactly selected voxel.

After the first seed cell and its coordinate are identified, the coordinate is inserted into the waltzing cubes seed queue at step 504. A seed queue stores coordinates of seed cells that are added and removed in subsequent steps.

At step 506, the seed queue is queried to see if it is empty. If the seed queue is empty, the waltzing cubes algorithm is terminated at step 520, since all cells that may produce a connected surface patch of the surface of interest have been analyzed and processed. If it is not empty, then the algorithm proceeds to the next step, and the main loop of the algorithm is entered, because all of the cells which may produce a connected surface patch have not been analyzed. Note that at the start of the algorithm, the only seed coordinate in the seed queue is the first seed cell coordinate added at step 504.

At step 508, a seed coordinate is removed from the seed queue. At step 510, using the seed cell coordinate, the waltzing cubes cell tree is queried for the corresponding seed cell. The cell tree identifies, organizes and stores all cells within the volume of data that belong to the surface of interest. Additionally, the cell tree maintains cell-to-cell vertex coherency data to ensure that exactly one calculation is made for each shared vertex that lies along the edge between surface patches in two adjacent cells.

The cell tree is structured to contain a set of buckets. A bucket is defined as a linear array of cells where subsequently added cells are appended at the end of the array. A bucket search for a particular cell is done in reverse order, starting with the cell at the end of the array and working back to the beginning. Alternative search algorithms, such as binary search, can be used. However, the reverse order linear search is optimal. Each bucket in the cell tree represents all examined cells within a subset of the volume, called a cell block. The volume is divided into cell blocks of optimal size, the size depending upon the ratio of surface patch producing cells to the total number of cells within the block. An increase in the volume size results in an increase in the number of blocks because the block size remains the same. Typically, a cell block size of 16×16×16 (4096 cells) is near optimal.

At step 512, if the seed cell exists in the cell tree, it has been previously examined, so it is ignored, and the loop continues by returning to step 506. If the seed cell does not exist in the cell tree, it has not yet been examined and processed, so it is inserted into the cell tree at step 514.

At step 516, a surface patch comprised of triangle primitives for the seed cell is produced. The surface patch can be generated by using the seed cell configuration and the corresponding triangulation table for that configuration. The triangulation can be an isosurface patch that has been pre-constructed for each cell configuration and stored in a triangulation table. Alternatively, the triangulation can be a variable-threshold surface patch that is created dynamically using local thresholds, adaptive thresholding or other criteria. The triangulation process uses the cell-to-cell vertex coherency data to reuse vertices computed by other cells and to create new vertices that are not yet computed. The triangulation may produce surface patches that are contained entirely within the seed cell or that span the seed cell and its adjacent cells in the cell tree.

At step 518, the adjacent cell coordinates are determined for the seed cell using the seed cell configuration and the corresponding adjacency table for that configuration. An adjacent cell coordinate is the cell coordinate for the corresponding cell that lies adjacent to the seed cell. Each seed cell has up to 6 adjacent cells, and therefore, up to 6 adjacent cell coordinates. An adjacency table contains, for each seed cell configuration, a pre-analyzed list of adjacent cell coordinates that identify cells that each produce a surface patch that is connected to the surface patch produced by the seed cell. Each of these adjacent cell coordinates is used to query the cell tree to determine whether it has already been examined. If it has been examined, the adjacent cell coordinate is discarded. If it has not been examined, the adjacent cell coordinate is inserted into the seed queue. The algorithm loops back to step 506. When the algorithm terminates at step 520, a wireframe model of a complete surface is produced.

The waltzing cubes method enables the run-time memory required to create the surface of interest to be significantly reduced. Specifically, the memory required is directly proportional to the number of cells that must be analyzed. Since the waltzing cubes method divides the volume of data into cell blocks, entire buckets of cells may be pruned (deleted) once it is known that the cell data is no longer needed. Accordingly, since only those cells which produce surface patches that are a part of the surface of interest are examined, the waltzing cubes method typically examines a small fraction of the total number of cells within the volume, resulting in an algorithm that is fast and efficient.

After the wireframe model has been generated at step 38a or 38b of FIG. 1, connectivity matrices are determined at step 39. The connectivity matrices are data structures which provide information regarding the connectivity between the vertices and polygons which comprise the wireframe model. The connectivity matrices are determined by traversing the polygon and vertex lists associated with the wireframe model, generating sets of immediate neighbor vertices and triangles associated with each vertex and polygon in the lists. For example, the vertex to polygon connectivity matrix contains, for each vertex in the wireframe model, a list of all polygons that contain that vertex. Likewise, a polygon to polygon matrix lists all adjacent polygons for each polygon in the model.

Using these connectivity matrices, the polygon list of the wireframe model is then re-ordered. The polygons generated using the variant of marching cubes are usually added to, and as such ordered in, the polygon list as the three dimensional volume is traversed. Accordingly, all of the polygons between the first and second images are generated first, followed by the polygons between the second and third images, and so forth. This polygon ordering is not intuitive, nor ideal for analysis or manipulation of the geometry at the local connectivity level. Consequently, in order to group vertices into populations and to analyze the populations, it is advantageous to re-order the polygons into the sequence by which they would be encountered while "traveling" through the lumen of the wireframe model. In addition, the re-ordering facilitates rapid three-dimensional renderings, since hidden objects or objects outside of the field-of-view can be easily identified and removed, thereby reducing the number of polygons rendered and thus increasing the rendering speed.

After connectivity matrices are computed, a normal vector is calculated for each vertex in the wireframe model at step 40a of FIG. 1. The direction of each normal vector is perpendicular to a plane that is tangent to the isosurface at each such vertex, typically pointing away from the object or away from the lumen of a body organ. The normal vectors at the respective vertices can be computed as the average of the normal vectors associated with each polygon connected to that vertex. The normal vector associated with a polygon is calculated using a vector cross product.

The wireframe model is refined using a geometric deformable model at step 40b. In a geometric deformable model, a surface is treated as a wave front that propagates in space over time until a targeted boundary is reached. With respect to the wireframe model, each vertex of the wireframe model is moved along its normal vector direction at a speed that is a function of both the surface curvature and the doubt (or confidence) level of a boundary estimate at that point. The surface evolves under this type of motion until the targeted boundary is reached, at which time the speed of motion approaches zero. Formally, if S(0) is an initial smooth surface and S(t) is a one-parameter family of surfaces generated by wave front propagation, the surface S should satisfy the following flow equation:

$$\frac{\delta S}{\delta t} = (\phi H - \nabla \phi \cdot \vec{N})\vec{N} \quad (1)$$

where H denotes the mean curvature, $\vec{N}$ is a unit normal vector, and (θ) is a positive differentiable function defined in three-dimensional space that acts as a stopping function (i.e., (θ) approaches zero as the surface nears the targeted boundary).

Figure 3A:
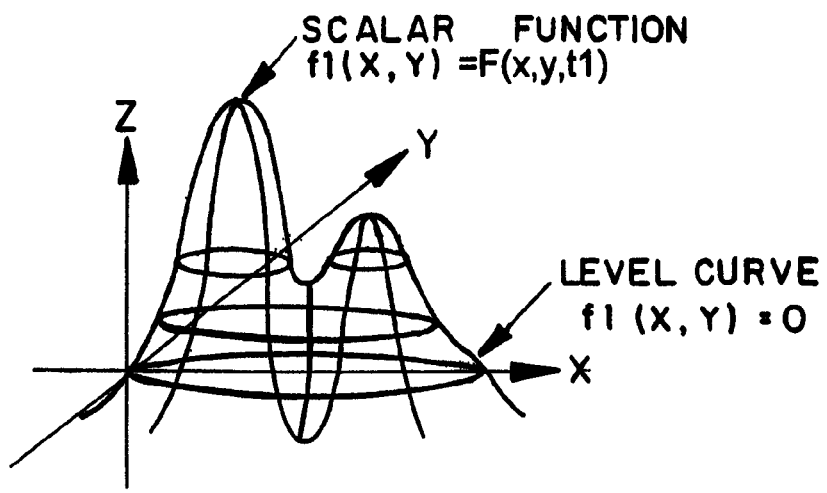
FIGS. 3 a-b are graphical representations of a method for treating evolving surfaces as the level surfaces of an evolving scalar function.
Figure 3B:
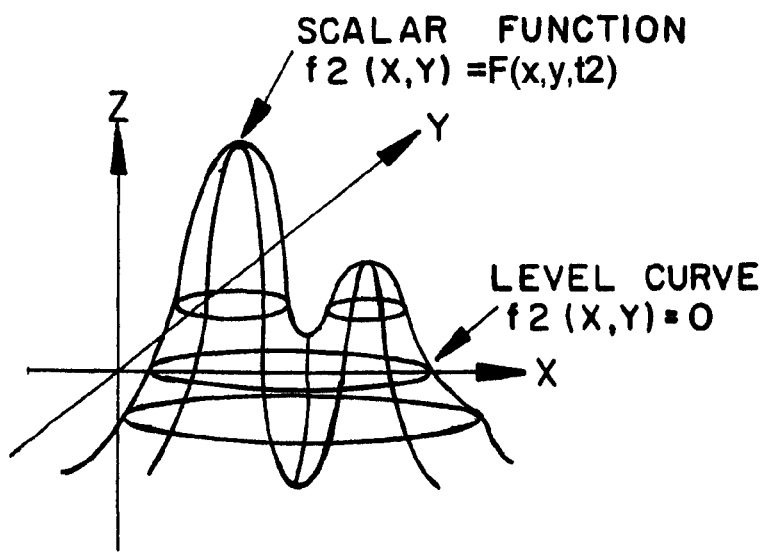

A direct solution for this equation is difficult because of the topology changes and singularities that are created during the course of surface evolution. Accordingly, special techniques are typically used to facilitate convergence of Eqn. (1). For example, a level-set technique can be used, such as the one proposed by Osher and Sethian in "Fronts propagation with curvature dependent speed: algorithms based on Hamilton-Jacobbi formulations", J. Computational Physics, 1988, 79: 12-49, which is hereby incorporated by reference. In the level-set approach, the surface S is embedded as a level surface $\Psi=0$ in a three-dimensional scalar function $\Psi$. The evolving family of surfaces S(t) is then generated from the level surface of an evolving family of scalar functions $\Psi(t)$. As shown in FIG. 3, evolving contours are treated as zero-level curves of the evolving function F. By shifting the scalar function F downward from time t1 to time t2 and extracting the zero level curves, the net effect of shrinking the circular contour (FIG. 3($a$)) is achieved (FIG. 3($b$)). If F is shifted down even further, the circular contour will appear to split into two smaller segments.

For the embedded level-surface to evolve according to Eqn (1), the scalar function $\Psi$ should evolve according to the equation:

$$\frac{\delta \Psi}{\delta t} = \phi \|\nabla \Psi\| \left( div\left(\frac{\nabla \Psi}{\|\nabla \Psi\|}\right) + v \right) + \nabla \phi \cdot \nabla \Psi. \quad (2)$$

The divergence operator $$div\left(\frac{\nabla \Psi}{\|\nabla \Psi\|}\right)$$

computes the mean curvature H of the embedded level surface from the scalar function $\Psi$. The constant, v, determines if the surface evolves inwardly or outwardly. The stopping function, $\phi$, can be defined as:

$$\phi = \frac{1}{1 + \|\nabla G_\sigma * I\|}$$

where $G_\sigma$ is a Gaussian filter whose characteristic width is $\sigma$ and * denotes a convolution operator. Images convoluted with the Gaussian filter before gradient computation are smoother and produce more accurate results. The purpose of the Gaussian filter is to smoothly force the evolution speed to zero at points where high intensity gradients exist.

More generally, the stopping function can be characterized as a doubt function that approaches 0 when there is no doubt that the wave has reached a boundary and 1 otherwise. Using this characterization better stopping functions can be designed so that they incorporate not only edge gradient information, as in Eqn (2), but also other critical information such as noise model and scale level. Furthermore, Bayesian statistical models can be used to properly define the doubt function since many factors contribute to one's doubt (or confidence) about any point being on a boundary.

Traditionally, a major problem associated with the use of geometric deformable models has been poor computational efficiency due to the fact that multiple iterations are required at numerous grid points. One approach to improve the computational efficiency has been the use of narrow-band or tube methods as described by Malladi et al. in "Shape modeling with front propagation: a level set approach", IEEE Trans. Pattern Analysis and Machine Intelligence, 1995, 17:158-175, which is hereby incorporated by reference. Although useful in some applications, the narrow-band method is inefficient when dealing with large wireframe models, such as those representing a colon. Accordingly, special constraints may need to be added to reduce the processing time for large, objects. In one embodiment, a three-dimensional region-growing model is used as a starting point for the deformable model approach. Alternatively, the deformable model approach may be applied to a low resolution dataset to produce an intermediate wireframe model. The intermediate wireframe model is then translated to a higher resolution dataset. Further, since the original volume of data typically has a high spatial resolution, the deformable model approach can be applied to a subsampled volume (e.g., one-eighth of the original volume of data) to produce an intermediate wireframe model without significantly affecting the shape of the rendered image. The intermediate wireframe model is then applied as a starting point for processing of the complete volume of data.

The vertices of the wireframe model can be analyzed and grouped into populations having abnormal wall structure as shown at steps 41-45 in FIG. 1.

The wall thickness of the structure at each vertex is measured at step 41. The wall thickness at a given vertex can be determined by measuring the distance from the inner surface of the selected object to its outer surface or some other position between the inner and outer surfaces. For body parts such as the colon or airways, the selected structure's wall is composed of soft tissue and the lumen of the structure comprises gas. Accordingly, the inner surface corresponds to a gas/soft tissue interface. Further, the colon and airways are typically surrounded by fat, gas, or other non-soft tissue material (i.e., contrast-enhanced blood vessels, bone, or calcification). Accordingly, the outer surface corresponds to the soft tissue/gas, soft tissue/bone, soft tissue/fat, or other such interface. The X-ray attenuation factors for room air (approximately −1024 HU to −425 HU), fat (about −200 HU to −20 HU), and other non-soft tissue structures such as contrast-enhanced blood vessels and bone (approximately >100 HU) are distinct from the soft tissue component (about 20 HU to 100 HU) of the airways or colon wall. Accordingly, the wall thickness at a vertex on the wireframe model can be calculated from the volume data of the selected organ, which can be measured at regularly spaced intervals along each normal vector. Alternatively, wall thickness can be estimated by analyzing differential characteristics of the intensity profile along the normal direction. For example, the transition from gas-filled lumen to wall tissue and then from wall tissue to fat or other software tissue can be captured by finding the first two peaks in the gradient of the intensity profile.

Referring to FIG. 6, a wall thickness at a vertex can be calculated by analyzing the intensity profile along the normal vector originated at the vertex. An intensity profile of a vector is defined as an array of interpolated x-ray attenuation factors (voxel values) along regularly spaced intervals along a vector originating at the vertex. The analysis of the intensity profile may include several heuristics depending upon the intensity profile type. One simple heuristic is to measure the thickness as the distance between the vertex and the point at which the attenuation factor drops below that of air (−425 HU) as seen in FIG. 6$a$. Another heuristic is to measure the thickness as the distance between the vertex and the point at which the attenuation factor exceeds above that of soft tissue (60 HU) as seen in FIG. 6$b$. Yet another heuristic is to measure the thickness as the distance between the vertex and the point at which there is a local minimum as seen in FIG. 6c. These heuristics are often too basic and are insufficient to accurately determine complex intensity profiles such as that in FIG. 6d. Therefore, a more mathematical analysis of the intensity profile is required for accurate wall thickness calculation. The advanced analysis include differential characteristics of the intensity profile, discrete first/second/third degree gradiant profiles, polynomial curve fitting along the intensity profile and solutions to differential equations based on the curve, and other knowledge based methodology. For optimal wall thickness measurement, a weighted combination of basic and advanced analysis is employed, and the results are averaged and normalized to reduce inaccuracies. Alternatively, the wall thickness at the vertex on the wireframe model can be calculated from the volume of data of the selected organ near the vertex. For example, another approach to estimate wall thickness is to classify the voxels in the vicinity of the segmented lumen surface into a small number of intensity groups. The shape of the resulting groups can be analyzed to determine the voxels that belong to wall and the wall thickness can then be estimated from these voxels.

Since the wall thickness of body structures such as the colon may be inadvertently or artificially increased, such as during musculature contraction of the colon at certain positions along the colon structure, many of the regions of abnormal thickness may not be indicative of true lesions. Instead, the thickened regions may represent normal structural elements, such as regions where the colon is contracted or where it touches solid organs. Accordingly, it can be beneficial to further analyze and characterize each vertex associated with abnormal thickness to refine the list of potentially abnormal vertices. Additional local shape features, computed at step 42, can be used to characterize and associate vertices as being abnormal.

For example, a local convexity value at each of the surface vertices can be determined at step 42. The local convexity values can be determined for all vertices, or for only those vertices associated with abnormal wall thickness. For each vertex, its neighboring vertices within a connected neighborhood of a pre-determined size (e.g., 3), is determined using the connectivity matrices. A local convexity value for each vertex, v, is computed as:

$$C = \sum_{i=1}^{n} D(v_i)$$

wherein $D(v_i)$ is the distance from the $i^{th}$ neighboring vertex to a plane through v and perpendicular to v's normal vector, and n is the number of neighboring vertices. Vertices associated with a convexity value of greater than a pre-defined maximum (e.g., >2) can be considered abnormal.

In addition, the local curvature at each vertex in a population can also be determined at step 42. The curvature reflects another shape feature of the object's surface at a given vertex. Vertices associated with broad curvatures indicate regions that are relatively flat. Accordingly, if the user wishes to identify only regions having thicknesses that vary significantly over short distances, those vertices with small curvatures may be labeled as abnormal.

The local curvature at each vertex in a population can be determined by summing the scalar distance between each of a user-determined number of levels, N, of adjacent vertices and the plane perpendicular to the normal of the vertex. The result is then normalized by the surface area outlined by the $N^{th}$ level of adjacent vertices. Because the direction of the curvature is ignored, the technique is able to detect areas of small curvature.

Figure 13:
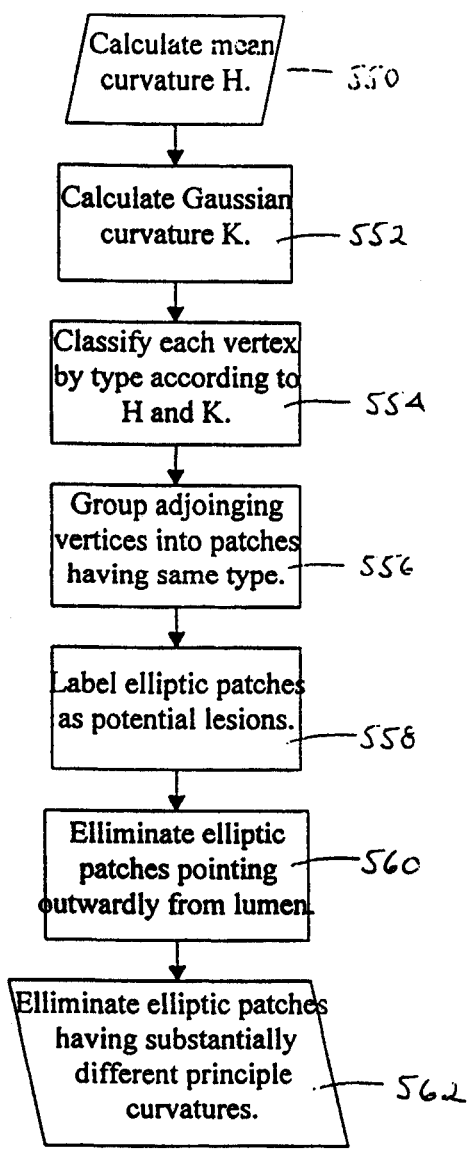
FIG. 13 is a flowchart representing an alternate method for analyzing the shape of a population.

Alternatively, local curvature can be computed at each vertex from the wireframe model represented as a level surface. In particular, as shown in FIG. 13, the mean curvature at each vertex of the wireframe model is determined at step 550. The mean curvature H (i.e., the average of the two principal curvatures) of the level surface $\Psi$ is given by:

$$H = \frac{\Psi_{xx}(\Psi_y^2 + \Psi_z^2) + \Psi_{yy}(\Psi_x^2 + \Psi_z^2) + \Psi_{zz}(\Psi_x^2 + \Psi_y^2) - 2\Psi_x\Psi_y\Psi_{xy} - 2\Psi_y\Psi_z\Psi_{yz} - 2\Psi_x\Psi_z\Psi_{xz}}{2(\Psi_x^2 + \Psi_y^2 + \Psi_z^2)^{3/2}}.$$

The Gaussian curvature K is similarly determined according to the equation at step 552:

$$K = \frac{\begin{vmatrix} \Psi_x^2(\Psi_{yy}\Psi_{zz} - \Psi_{yz}^2) + \Psi_y^2(\Psi_{xx}\Psi_{zz} - \Psi_{xz}^2) + \\ \Psi_z^2(\Psi_{xx}\Psi_{yy} - \Psi_{xy}^2) + 2\Psi_x\Psi_z(\Psi_{xy}\Psi_{yz} - \Psi_{xz}\Psi_{yy}) + \\ 2\Psi_x\Psi_y(\Psi_{xz}\Psi_{yz} - \Psi_{xy}\Psi_{zz}) + 2\Psi_y\Psi_z(\Psi_{xz}\Psi_{xy} - \Psi_{xx}\Psi_{yz}) \end{vmatrix}}{2(\Psi_x^2 + \Psi_y^2 + \Psi_z^2)^{3/2}}.$$

Each vertex of the wireframe model can be classified as one of four types at step 554. The point is classified as elliptic if $K(p)>0$, as hyperbolic if $K(p)<0$, as parabolic if $K(p)=0$ and $H(p)\neq 0$, or as planar if $K(p)=0$ and $H(p)=0$. This classification scheme enables the vertices to be grouped into patches having vertices having the same characteristic shape at step 556. Since polyps protrude into the colon lumen, only elliptic patches are labeled as representing likely polyps at step 558.

Additionally, elliptic patches that point outwardly from the colon are eliminated at step 560 using the signs of the two principle curvatures, $k_1$ and $k_2$. The principal curvatures, $k_1$ and $k_2$, are derived from the mean and Gaussian curvatures to be $k_1=H+\sqrt{H^2-K}$ and $k_2=H-\sqrt{H^2-K}$. Only when $k_1$ and $k_2$ are both negative (or positive depending on coordinate system used) does the elliptic patch represent a potential lesion pointing inward with respect to the lumen.

At step 44, vertices representing an abnormality are selected. Those vertices meeting selected criteria can be identified as abnormal vertices. For example, vertices having abnormal thickness and/or convexity and/or curvature criteria may be identified as abnormal vertices. In a specific application, the wall thickness values, local convexity values, and local curvature values can be used, independently or in conjunction with each other, to either accept or reject vertices as being abnormal. The individual parameters can be combined using a logical AND operation.

At step 45, the vertices on the wireframe model associated with abnormal structure (i.e., having a combination of associated abnormal wall thickness and/or abnormal shape, such as abnormal local convexity and/or abnormal local curvature) are grouped into populations. The re-ordered connectivity matrices are used to determine if vertices associated with abnormal parameters are directly connected to other vertices that are also associated with abnormal parameters. Accordingly, each formed population represents a potential abnormal lesion. In addition, each population can be further analyzed and characterized by its size, dimensions, or other statistical quantities.

Figure 8:
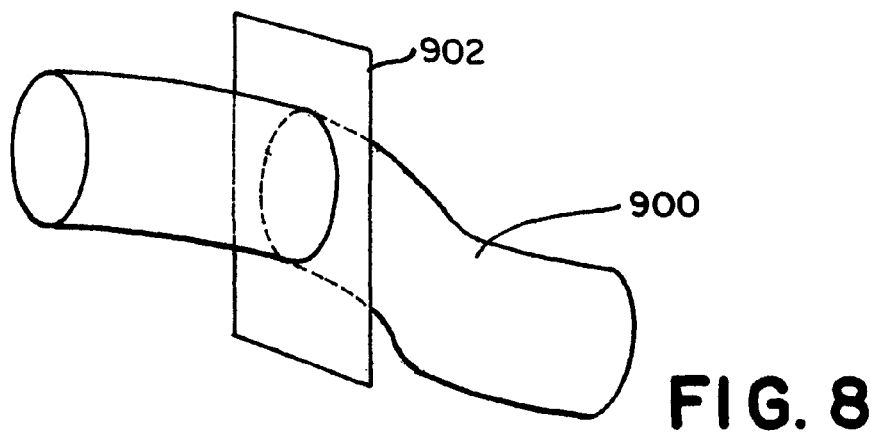
FIG. 8 is a schematic diagram depicting the cross-sectional area of a lumen defined by a plane through the lumen.
Figure 9A:
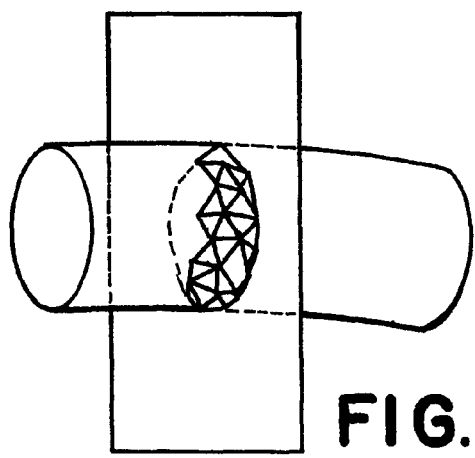
FIGS. 9 a-d are diagrams representing methodology for calculating the cross sectional area of the lumen defined by the cutting plane shown in FIG. 8.
Figure 9B:
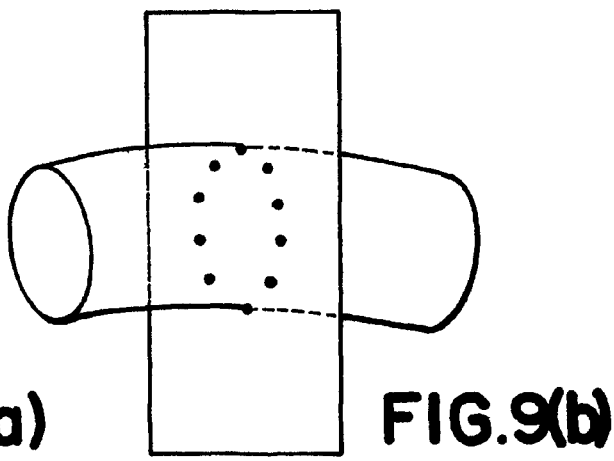
Figure 9C:
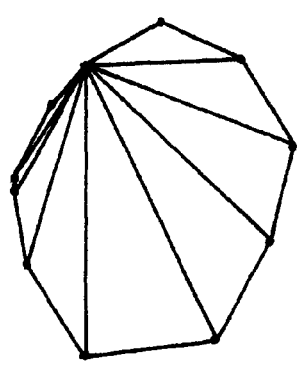
Figure 9D:
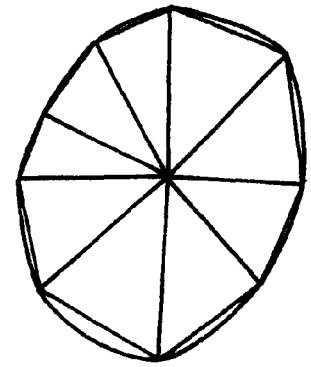

A cross sectional area (CSA) of surface model is defined as the area outlined by the contour formed by the interaction of the surface model 900 with an arbitrary CSA plane 902 as shown in FIG. 8. The cross sectional area at the site of a lesion may be used to calculate the degree of stenosis, or narrowing, caused by the lesion at that location. The cross sectional area may also be used with a central path algorithm to determine areas of stenosis in a lumen of an organ. The surface model is represented as a wireframe mesh of triangles. Using the connectivity matrices, all triangles in the wireframe which intersect the CSA plane are identified as shown in FIG. 9a. For each triangle, edges of the triangle which intersects the CSA plane are identified, and intersecting vertex point between each edge and the CSA plane are computed. The set of these intersecting vertex points represents an approximation of the cross sectional area which is to be computed, and it is defined as the CSA contour. The CSA contour lies completely in the CSA plane as shown in FIG. 9b. The CSA contour vertices are used to triangulate a set of adjacent triangles that span the entire contour. The triangulation may simply define the edges of each triangle as consecutive contour vertices as shown in FIG. 9c. Alternatively, a centroid point for the contour may be computed and used for a more accurate triangulation as shown in FIG. 9d. Because the generated triangles span the contour, the cross sectional area of the contour is simply defined as the sum of the areas of each triangle within the contour. This method is a numeric approximation that is sufficiently close to the true cross sectional area.

Each population is further analyzed according to aggregate shape features at step 46 to reduce the occurrence of false positive findings. Since the structure of body organs may appear abnormal, either inadvertently or artificially, such as during muscular contraction of the colon at certain positions along the colon's structure, many of the abnormal populations may not be indicative of true lesions. Instead, these populations may represent normal structural elements, such as regions where the colon is contracted or where it touches solid organs. Accordingly, it may be advantageous to further analyze and characterize each population identified as having an abnormal structure to further refine the list of potential lesions and to increase the likelihood that a detected population represents a true abnormality.

For example, the shapes of the populations can be analyzed, characterized, and accepted or rejected as being abnormal as illustrated in detail in FIG. 2. At step 120 a centroid for each population is calculated. The centroid can be computed as a weighted sum of the positions of each vertex within the population. The individual vertices can be weighted by their associated wall thickness values or other parameters. Once the centroid has been determined for a population, the height and normal vector for that population can be determined.

A population normal vector is calculated for each population at step 121. The population normal vector can be computed as a sum of the normal vectors at each of the vertices within the population, and the individual vertex normal vectors can be weighted by their corresponding wall thickness values or other parameters.

Figure 5:
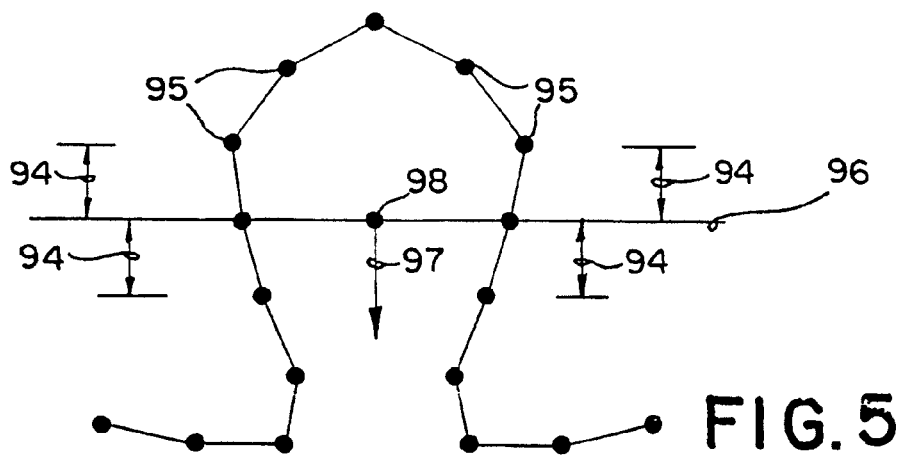
FIG. 5 is a schematic representation of a two-dimensional plane through a wireframe model of an area of abnormal wall structure illustrating a method for determining the convexity of the area.

The convexity value, (C), for each population is determined at step 122. The convexity is a measure of the direction and magnitude of the shape of the surface of the population. As shown in FIG. 5, the convexity of a population is computed as the sum of the distances 94 from vertices 95 in the population to a plane 96, perpendicular to the population normal vector 97 passing through the centroid 98, according to the equation:

$$C = \sum_{i=1}^{n} D(v_i)$$

wherein $D(v_i)$ is the distance from the $i^{th}$ vertex of the population to the plane 96 and n is the number of vertices 95 within a predetermined space relative to the centroid. Since the normals at each vertex are typically assigned to point away from the center of the object, or the lumen of the object, a population which protrudes into the lumen of the object would have a positive convexity value, whereas a population that projects away from the lumen would exhibit a negative convexity value. When the structure is a colon, populations with a negative convexity value are excluded from being considered abnormal, since abnormal colon masses tend to project into the lumen of the colon and would have a positive convexity value.

Further, the higher the magnitude of the convexity value, the greater the slope of the surface of the population. When the structure is a colon, only populations having a positive convexity value above a minimum value are reasonably expected to be potential lesions, since some cancerous colon masses are generally manifested by steeply sloped growths that protrude into the lumen of the colon.

The height (H) of each population is determined at step 123. The height is calculated as the difference between the distance of the vertex farthest from a plane 96, perpendicular to the population normal 97 and passing through the centroid 98, and the distance of the vertex closest to that plane according to the equation:

$$H = \text{MAX } D(v_i) - \text{MIN } D(v_i).$$

The height provides an indication as to whether a population is reasonably expected to be a true lesion since populations with large heights are more likely to represent abnormal masses.

The principal curvatures, $k_1$ and $k_2$, can also be used to reduce the likelihood of false positive identifications. Generally, polyps are nearly symmetrical and, accordingly, patches representing true polyps are likely to arise when the two principal curvatures on the top of a potential lesion are similar. Further, normal colon haustra have ridge-like shapes and, therefore, potential lesions having principal curvatures, $k_1$ and $k_2$, which are substantially different are eliminated as likely polyps at step 562.

Other shape features may be used to include or exclude populations in the list of potential lesions. For example, if a population has a long axis dimension that is greater than a multiple (e.g., 10 times) of the short axis dimension, and the short axis dimension is, for example, less than 5 mm wide, then the population might be considered to be normal. Further, a potential lesions "roundness" could be quantified and used to rank potential lesions. Likewise, weighting wall thickness determinations with shape features may provide valuable heuristics for classifying potential lesions. Accordingly, the shape features discussed herein are included only by way of example, and are not intended to limit the scope of the invention.

Referring again to FIG. 1, after the populations with abnormal wall structure (i.e., wall thickness, convexity, or other shape features) have been identified and characterized, populations that fail to meet certain criteria are eliminated as potential lesions at step 48.

At step 50, those populations which are still considered to represent potential lesions are sorted and arranged in an electronic listing. The listing can be sorted according to such properties as size, convexity, curvature, height, mean wall thickness, standard deviation of wall thickness, other statistical quantities, or a combination of such parameters (e.g., the product of the group convexity value, C, and the group height value, H). Each population in the listing could be linked to a three-dimensional camera position that best illustrates it in the three-dimensional display. Accordingly, the user can choose a population from the listing and thereby be presented with a view of the abnormal area as it appears in the three-dimensional rendering. One means of linking the population to a three-dimensional rendering camera position is by providing the user with a three-dimensional camera view of the population that is parallel to the population normal and centered on the centroid of the population, and set at a chosen distance from the centroid. In one embodiment, the user is presented with two views of the selected population, one from an external perspective and the other from an internal perspective (i.e., from within the lumen of the structure). Lesion locations, either identified manually by a user or by the above algorithms can also be used to generate lesion maps, i.e., two dimensional or three dimensional renderings of entire colon with lesion sites marked.

A three-dimensional rendering of the wireframe model is displayed at step 51. In one embodiment, the user can navigate through a three-dimensional rendering of the wireframe model which is displayed on the monitor 28. The detected abnormal populations are displayed with a contrasting color scheme to distinguish them from the remainder of the rendered structure, so that the abnormal populations can be quickly and easily identified by human visual inspection. Further, the color scheme can reflect variations in wall thickness, convexity, or curvature, or some other parameter. For example, the normal portions of the rendered structure can be displayed in shades of pink while the potentially abnormal populations are displayed in a rainbow of colors. More specifically, vertices could be assigned colors ranging from dark blue (for vertices with minimum abnormal thickness) to bright blue (for vertices with maximum abnormal wall thickness) to provide a stark contrast to the pinkish color assigned to the normal portions of the rendered structure.

In an alternate embodiment, the user is presented with a volume rendered display centered on the centroid of a selected abnormal population. For example, a volume-rendered view of a subvolume of user defined size centered on the centroid of the population can be displayed for visual inspection. Volume rendering is a visualization technique that creates a three-dimensional image using all of the volume data, rather than only an extracted surface representation. Traditionally, volume rendering is accomplished by projecting a series of rays from the user's viewpoint through the data volume. The color at each point (i.e., pixel) in the resulting three-dimensional image is determined by calculating a weighted sum of all voxels along each ray. This weighting factor is determined by a transfer function that is computed during a process called classification. Additionally, voxels belonging to a lesion may be selectively enhanced with color and/or opacity values.

Altering the transfer function during volume rendering can reveal different characteristics of the rendered data and, thus, it is often desirable to interactively reclassify and re-render the data. However, the rate at which images are rendered can be slow for data volumes as large as the ones typically used in medical imaging. Accordingly, it can be beneficial to use texture mapping to dramatically increase the rate at which volume rendering is performed. In texture mapping, volume data is considered to be a series of two-dimensional textures that are interpolated, projected, and displayed rapidly on a series of polygons using specialized computer hardware.

The texture mapped volume rendering method uses high-speed texture memory and blending hardware available on a Silicon Graphics' computer workstation to approximate the results of the more computationally expensive ray-casting algorithm. The volume data is first loaded into texture memory. The textures are then semi-transparently mapped onto a series of parallel two-dimensional rectangles that correspond to slices of the volume. The texture mapped rectangles are then drawn and blended to allow the user to see through the volume. The colors and transparencies of the resulting three-dimensional object are controlled by color and opacity transfer functions. The entire volume can then be viewed by stacking the texture mapped rectangles in the proper order and looking toward the stack. Since viewing the stack along one of its edges does not optimally display the volume, a new stack is generated which is orthogonal to the original stack. This new stack is then used to display the volume along an edge. Likewise, for any additional viewing, angles, additional stacks may be required. Generating the stacks is a dynamic process and each stack can be generated on an as needed basis. Texture mapping can use standard two-dimensional texture memory or faster three-dimensional texture memory.

In yet another alternate embodiment, upon selection of a population from the listing, the user can be presented with a three-dimensional, surface-rendered wireframe model of the population embedded within a volume-rendered display using texture memory techniques. Such a display is useful to show the three-dimensional relationships between the wireframe model and the volume data. Embedding a surface-rendered model inside a volume rendering can be accomplished using texture memory since both techniques use semi-transparent or opaque surfaces to generate their imagery. However, if the surface rendering is semi-transparent, care must be taken to ensure that all objects are blended in the proper order (typically, from back to front). All or part of the volume can be rendered. For example, to view a small structure using volume rendering, a subvolume of data surrounding that structure can be rendered, as opposed to displaying the entire volume of data. The point about which the subvolume rendering is performed can be selected manually by the user, or automatically by the above algorithms. It should also be appreciated that the multiplanar views and volume rendering can be combined in a similar manner.

If the user wants to view the results of the various rendering techniques using separate display windows, the user can clone the display window 200 so that the two (or more) display windows share the same data. However, each display window could render using different techniques (i.e., multi-planar display, surface rendering, volume rendering). Accordingly, the user could open a single window with all three rendering techniques and then clone the window three times to view each technique separately. Changes made to the data in any one of the connected windows would be propagated to all the cloned windows. Camera orientations could be synchronized between the separate windows to lock the views together. Position tracking techniques could show the camera position of one viewer in another, so that the user could follow the path of a three-dimensional camera moving inside the structure in one display window from an external perspective using a cloned display window with another three-dimensional camera from an overhead position.

Figure 7:
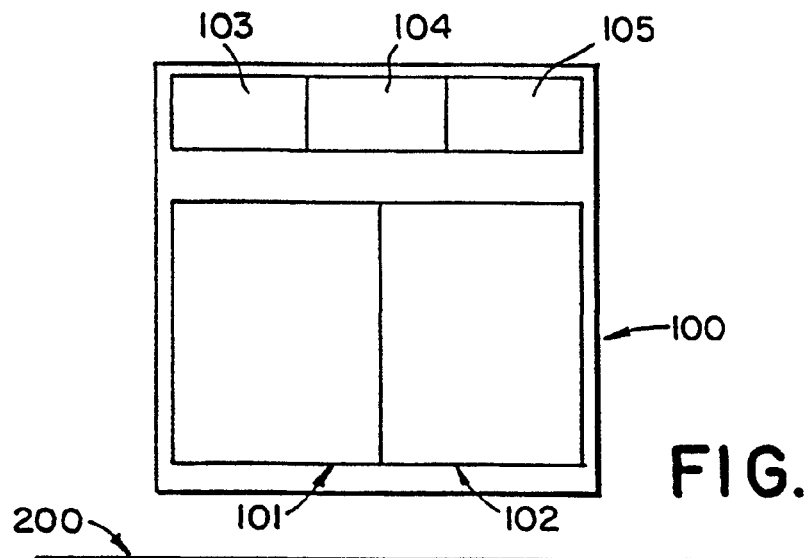
FIG. 7 is a schematic view of a display window for displaying a volume rendered image, a surface rendered image, and three multiplanar images along three different planes of a selected organ system.

An example of a computer console display 100 useful for displaying a three-dimensional rendering of a structure is shown in FIG. 7. The display 100 comprises a first window 101 for displaying a volume rendered image of the structure and a second window 102 for displaying a surface rendered image of the structure. Alternatively, the second window 102 can display a surface rendered image of the structure embedded within a volume rendered display, as described above. In addition, three multiplanar windows, 103, 104, and 105, are provided in a third window for displaying axial, coronal, sagittal, or oblique two-dimensional slices through the structure at a user-defined point, or at the centroid of a chosen population.

Figure 10:
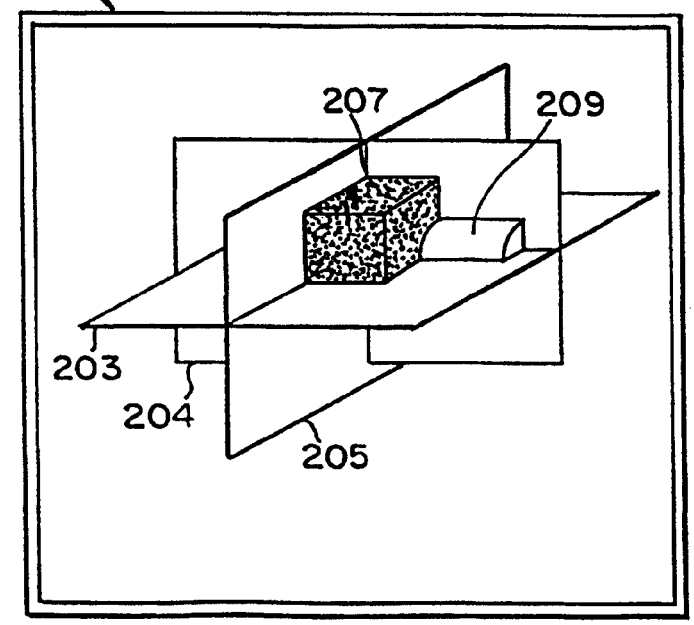
FIG. 10 is a schematic view of a display window for displaying a volume rendered image, a surface rendered image, and three multiplanar images along three different planes of a selected organ system combined in a single window display.

Alternatively a single window display 200, as shown in FIG. 10, can be used to display a three-dimensional rendering of the structure. The single window display comprises a single three-dimensional display window for presenting a combination of multiplanar images 203, 204 and 205 with a volume-rendered image 207 centered on a point located within a surface-rendered image 209. The display presents a holistic view of all the data that can aid in the visualization and understanding of the inter-relationships of the various rendering techniques (i.e., surface rendering, volume rendering, and intersecting two-dimensional planes). The various rendering techniques can exist together because they are all based on the same patient coordinate system supplied by the image scanner, and they are all rendered using shared three-dimensional graphics techniques (texture memory) and a common graphics library. The intersecting planes can be rendered as opaque textures (as opposed to semi-transparent textures used in volume rendering) mapped onto two-dimensional rectangles using texture mapping and drawn in their proper orientation. The user can interactively scroll through slices parallel to any of the intersecting planes and can view any combination of planes (e.g., axial and/or sagittal and/or coronal planes), or the user can create and view an oblique slice plane. The planes can be rendered together with the surface data to show the exact relationship between the wireframe model and the volume (by viewing the intersections and orientations of the surface rendered wireframe model and the two-dimensional slices). They can be viewed together because the planes are rendered as any other kind of surface (i.e., a flat, two-dimensional rectangle).

Figure 14:
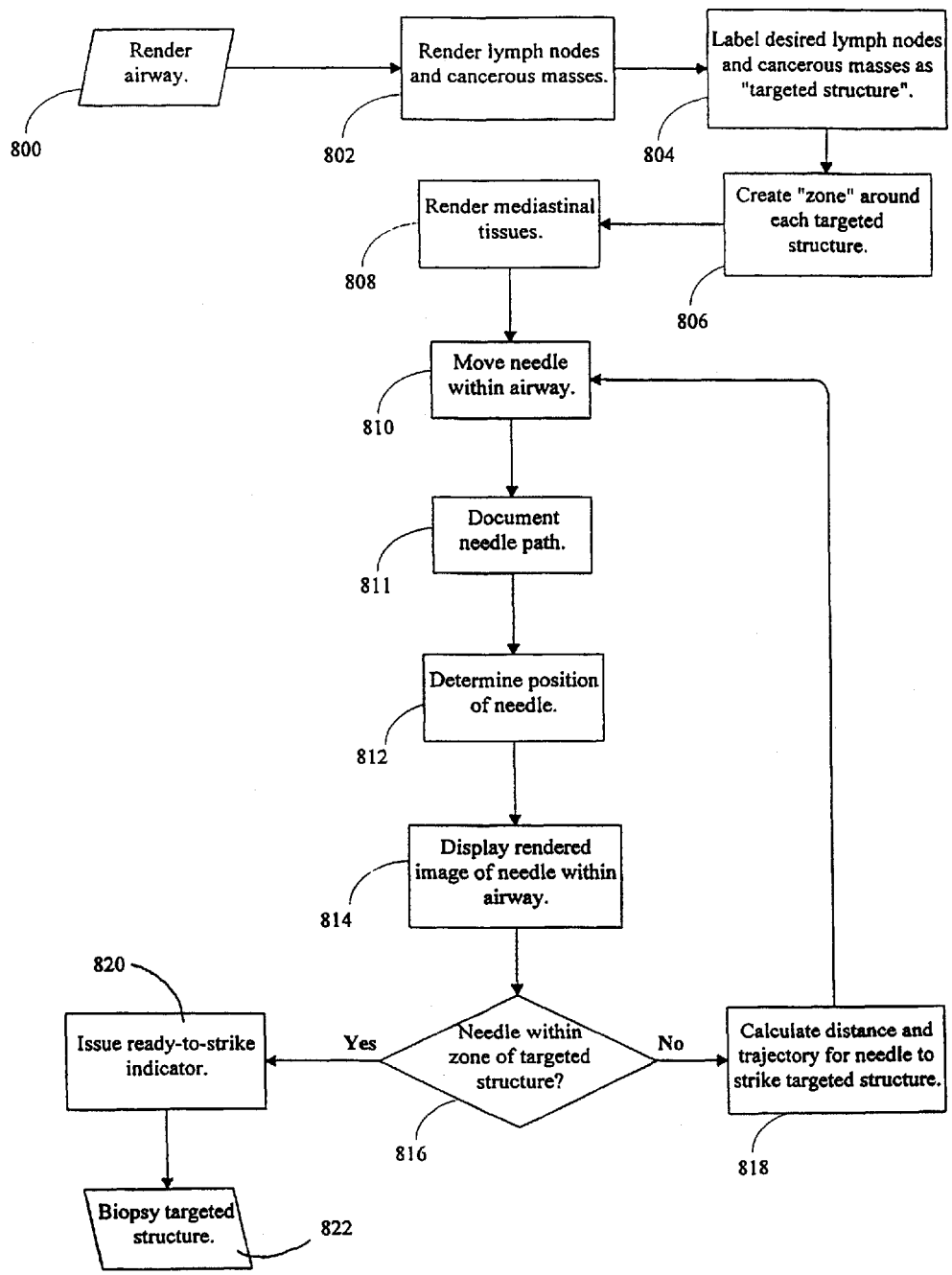
FIG. 14 is a flowchart representing a method for guiding endoscopic biopsy procedures in accordance with the present invention.

The method and system of the present invention can also be used to guide needle biopsy procedures of diagnosed lesions as illustrated in FIG. 14. One example is biopsy guidance of cancerous lymph nodes in patients with lung cancer via transbronchial needle aspirations (TBNA). At steps 800 and 802, the patient's airway, lymph nodes, blood vessels, and any cancerous masses are segmented and rendered in a three-dimensional display. The rendering is performed as described above. Of course, the structures must be accurately rendered in order to provide a reasonable likelihood that the procedure will be successful. An alternative approach to automatically rendering segmenting the lymph nodes and/or the cancerous masses from the volume data, spherical "targets" can be manually placed within lesions at lesion locations previously identified on the multiplanar data images to indicate the position and approximate size and shape of the targeted object. Alternatively, irregular targets can be modeled by having the user free-hand draw regions of interest on the multi-planar images from which three-dimensional targets can be rendered.

Once the lymph nodes and cancerous masses have been identified and rendered, each lymph node and cancerous mass which is to be biopsied is labeled as a "targeted structure" at step 804. A zone, or striking distance, is then defined around each of the targeted structures in step 806. The zone represents a volume of space surrounding the targeted structure which is sufficiently close to the structure to enable a biopsy needle to reach the targeted structure and biopsy tissue from the targeted structure. At step 808, blood vessels and other mediastinal tissues may be rendered. Rendering of the mediastinal tissues is performed because it is important to avoid puncturing major blood vessels during the needle biopsy procedure.

An endoscopic biopsy procedure, such as TBNA, is performed with the actual biopsy needle retracted within the instrument channel of an endoscope while the endoscope is inserted in the airway. As soon as the endoscope tip is within striking distance of a pre-selected target, the needle is extended into the target and then retracted back into the endoscope's instrument channel, hopefully containing a sample of tissue. Unfortunately, doctors often make "blind" biopsies into tissue since they cannot visually see through an opaque organ, hence the purpose of computer-simulated guidance. "Striking distance" is defined as the maximum distance from the target that the endoscope tip can located in order to obtain an adequate sample when the needle is extended. In clinical practice, this distance should be at most half the length of the needle—½ cm for a 1 cm needle—so that when the needle is extended a sample of at least the needle length is obtained. Also, both the scope's position and orientation must be taken into account to decide if the needle will be able to effectively biopsy the target, otherwise, if the scope tip is within striking distance but pointed away from the target, then the extended needle will not hit the target. If the tip is not pointed directly at the target but is pointed at an oblique angle to the target, the needle may glance off the side of the target and not obtain an adequate tissue sample. And if the target's diameter is smaller than the needle length, there is a chance that the tip may completely penetrate the target and biopsy tissue on the other side of the target.

The simulated endoscope containing a biopsy needle within its instrument tract is then inserted into and moved within the patient's airway at step 810. As the simulated endoscope moves through the airway, the position of the tip of the needle is monitored at step 812. The monitoring can be done either on a continuous basis or intermittently. If desired, the movement of the simulated endoscope tip through the airway can be recorded and documented at step 811.

Once the position of the simulated endoscope tip with its needle is determined, a rendered image of the needle tip within the rendered image is displayed at step 814. Accordingly, the physician performing the biopsy procedure can visually monitor the movement of the simulated needle through the airway in relation to surrounding anatomy. In order to more realistically simulate the view that would be obtained using a conventional bronchoscope, the displayed image can be altered to reflect the distorted camera view of conventional bronchoscopes. In addition to displaying a rendered image of the simulated needle tip within the airway, an external view of the airway showing the position and orientation of the needle can be simultaneously displayed.

At step 816, it is determined whether the needle tip is within the zone, or within striking distance, of a targeted structure. If the needle tip is not within the striking distance of a targeted structure, then the distance and trajectory for the needle to reach a targeted structure is determined at step 818. The needle is then repositioned within the airway at step 810 using the calculated trajectory and distance as a guide for the movement of the needle.

However, if the simulated needle tip is within the striking distance of a targeted structure at step 816, then a ready-to-strike target proximity indicator is issued at step 820. The indicator serves to signal the physician to biopsy the targeted structure, at step 822. There are four types of target proximity indicators: (1) "getting close" indicator that increases in intensity as the endoscope tip approaches the target, (2) "strike zone" indicator that tells when the endoscope tip is within striking distance of the target and in the proper orientation to obtain an adequate tissue sample, (3) "too close" indicator that signals when the scope tip is too close to the target, and (4) "close, but no cigar" indicator that tells when tip is close enough to strike but is not pointing in the right direction for obtaining a good sample. In addition to these four indicators, a fifth type or alarm can be activated when the needle is in danger of penetrating vital organs near the target and putting the patient at risk.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

We claim:

1. A computer-implemented method for interactively displaying a three-dimensional rendering of a structure having a lumen comprising the steps of:
   a. forming a three-dimensional volume of data from a series of two-dimensional images representing at least one physical property associated with the three-dimensional structure;
   b. generating a wireframe model of a selected region of interest;
   c. deforming the wire frame model using a geometric deformable model to more accurately represent the region of interest; and
   d. rendering the wireframe model in an interactive three-dimensional display.

2. A computer-implemented method for interactively displaying a three-dimensional rendering of a structure having a lumen comprising the steps of:
   a. providing a three-dimensional volume of data representing at least one physical property associated with the structure having the lumen;
   b. generating a wireframe model having vertices representing a region of interest of the structure having the lumen;
   c. refining the wire frame model using a geometric deformable model; and
   d. rendering the wireframe model in an interactive three-dimensional display.

3. The method of claim 2 wherein the wireframe model comprises a plurality of vertices, the method comprising:
   grouping the vertices of the wireframe model into regions having a characteristic indicating abnormal structure;
   analyzing the regions having abnormal structure to identify regions having a high degree of abnormality; and
   rendering the wire frame model in an interactive three-dimensional display to indicate the regions having abnormal structure.

4. The method of claim 3 wherein the grouping step comprises:
   calculating a mean curvature at selected vertices;
   calculating a gaussian curvature at the selected vertices;
   classifying the selected vertices according to the mean curvature and the gaussian curvature; and
   grouping adjoining selected vertices into patches of same vertex classification.

5. The method of claim 4 wherein the analyzing step comprises labeling patches having an elliptical classification as a potential lesion.

6. The method of claim 5 wherein the analyzing step comprises eliminating from the grouping selected elliptical patches which point outwardly from the lumen.

7. The method of claim 6 wherein the analyzing step comprises calculating principal curvatures of the patches from the mean and gaussian curvatures and eliminating from the grouping any elliptical patches having substantially different principal curvatures.

8. The method of claim 2 comprising calculating a normal vector for each vertex in the wire frame model.

9. The method of claim 8 wherein the refinement step comprises moving each vertex of the wireframe model along its normal vector direction at a speed that is a function of a surface curvature and a doubt level of a boundary estimate at that point.

10. The method of claim 8 wherein the refinement step uses a three-dimensional region growing model as a starting point for the geometric deformable model.

11. The method of claim 2 wherein the step of generating a wireframe model comprises the steps of identifying a surface model of the region of interest and generating a wireframe model of the surface model.

12. The method of claim 11 comprising:
    grouping the vertices of the wireframe model into regions having a characteristic indicating abnormal structure;
    analyzing the regions having abnormal structure to identify regions having a high degree of abnormality; and
    rendering the wire frame model in an interactive three-dimensional display to indicate the regions having abnormal structure.

13. The method of claim 12 wherein the grouping step comprises:
    calculating a mean curvature at selected vertices;
    calculating a gaussian curvature at the selected vertices;
    classifying the selected vertices according to the mean curvature and the gaussian curvature; and
    grouping adjoining selected vertices into patches of same vertex classification.

14. The method of claim 13 wherein the analyzing step comprises labeling patches having an elliptical classification as a potential lesion.

15. The method of claim 14 wherein the analyzing step comprises eliminating from the grouping selected elliptical patches which point outwardly from the lumen.

16. The method of claim 15 wherein the analyzing step comprises calculating principal curvatures of the patches from the mean and gaussian curvatures and eliminating from the grouping any elliptical patches having substantially different principal curvatures.

17. The method of claim 2 comprising isolating the region of interest from the volume of data based on a selected value of the physical property representing the region of interest.

18. The method of claim 17 wherein the step of isolating comprises segmenting the region of interest.

19. The method of claim 18 comprising creating an isosurface of the region of interest.

20. The method of claim 19 wherein the step of generating a wireframe model comprises generating a wireframe model of the isosurface.

21. The method of claim 20 wherein, the wire frame model comprises a plurality of vertices, the method comprising:
    grouping the vertices of the wireframe model into regions having a characteristic indicating abnormal structure;
    analyzing the regions having abnormal structure to identify regions having a high degree of abnormality; and rendering the wire frame model in an interactive three-dimensional display to indicate the regions having abnormal structure.

22. The method of claim 21 wherein the grouping step comprises:
   calculating a mean curvature at selected vertices;
   calculating a gaussian curvature at the selected vertices;
   classifying the selected vertices according to the mean curvature and the gaussian curvature; and
   grouping adjoining selected vertices into patches of same vertex classification.

23. The method of claim 22 wherein the analyzing step comprises labeling patches having an elliptical classification as a potential lesion.

24. The method of claim 23 wherein the analyzing step comprises eliminating from the grouping selected elliptical patches which point outwardly from the lumen.

25. The method of claim 24 wherein the analyzing step comprises calculating principal curvatures of the patches from the mean and gaussian curvatures and eliminating from the grouping any elliptical patches having substantially different principal curvatures.

* * * * *